(12) United States Patent
Karasawa

(10) Patent No.: US 8,398,552 B2
(45) Date of Patent: *Mar. 19, 2013

(54) ULTRASONIC DIAGNOSTIC APPARATUS

(75) Inventor: Hiroyuki Karasawa, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 382 days.

This patent is subject to a terminal disclaimer.

(21) Appl. No.: 12/662,326

(22) Filed: Apr. 12, 2010

(65) Prior Publication Data

US 2010/0262005 A1    Oct. 14, 2010

(30) Foreign Application Priority Data

Apr. 14, 2009 (JP) ................................ 2009-097733
Apr. 20, 2009 (JP) ................................ 2009-101770

(51) Int. Cl.
*A61B 8/00* (2006.01)

(52) U.S. Cl. ................... 600/443; 600/407; 600/437

(58) Field of Classification Search ............ 600/407, 600/437, 443, 459
See application file for complete search history.

(56) References Cited

U.S. PATENT DOCUMENTS

| | | | | |
|---|---|---|---|---|
| 5,579,770 A * | 12/1996 | Finger | ........................... | 600/447 |
| 6,251,073 B1 | 6/2001 | Imran et al. | | |
| 6,674,373 B1 * | 1/2004 | Jones et al. | ...................... | 341/51 |
| 6,773,399 B2 | 8/2004 | Xi et al. | | |
| 2004/0263353 A1 * | 12/2004 | Imajo | ....................... | 340/870.07 |
| 2005/0004473 A1 * | 1/2005 | Fujita et al. | ................... | 600/476 |
| 2008/0114249 A1 * | 5/2008 | Randall et al. | ................. | 600/447 |

FOREIGN PATENT DOCUMENTS

| | | |
|---|---|---|
| JP | 2002-085405 | 3/2002 |
| JP | 2003-299648 | 10/2003 |
| JP | 2008-018107 | 1/2008 |

* cited by examiner

*Primary Examiner* — Tse Chen
*Assistant Examiner* — Joel F Brutus
(74) *Attorney, Agent, or Firm* — Jean C. Edwards, Esq.; Edwards Neils PLLC

(57) ABSTRACT

In an ultrasonic diagnostic apparatus for performing serial transfer between an ultrasonic probe and an apparatus main body, stable image formation can be performed even when transfer quality is poor while realizing downsizing of the ultrasonic probe. The apparatus includes: (i) an ultrasonic probe including a reception signal processing unit for generating parallel sample data based on reception signals outputted from plural ultrasonic transducers, a parallel/serial conversion unit for converting the parallel sample data into serial sample data, and a communication unit for transmitting the sample data; and (ii) an ultrasonic diagnostic apparatus main body including a storage unit for storing the sample data of at least one frame transmitted from the ultrasonic probe, and an image forming unit for generating an image signal by performing reception focusing processing on the sample data with respect to every one frame read out from the storage unit.

21 Claims, 17 Drawing Sheets

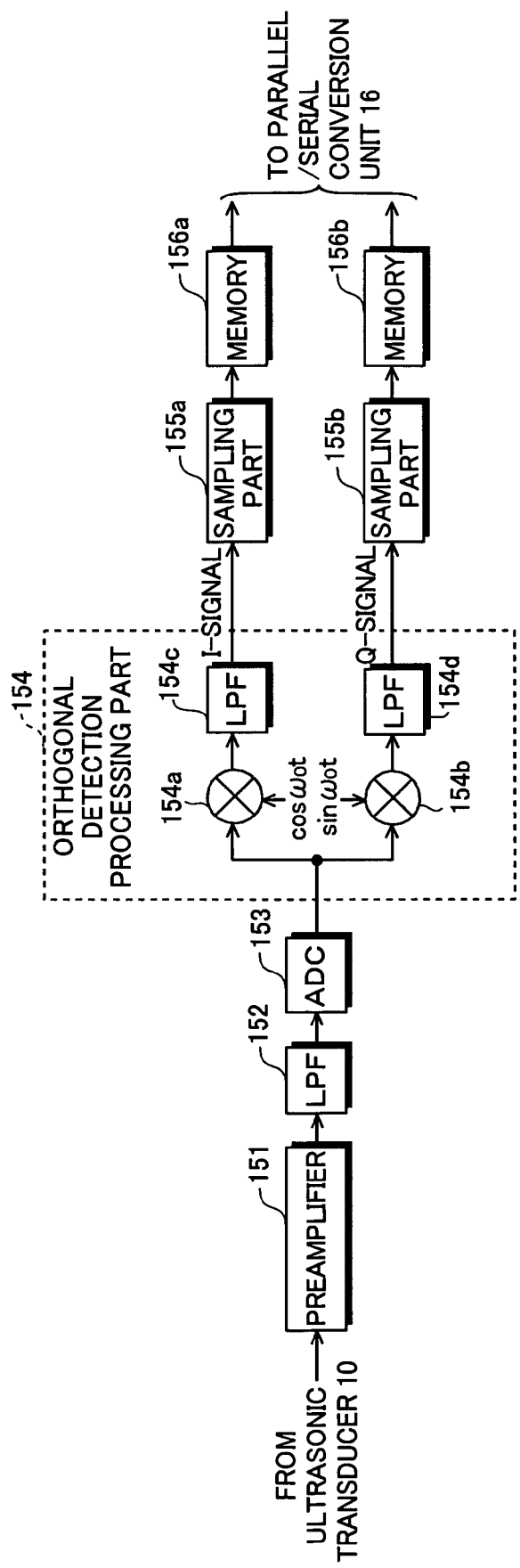

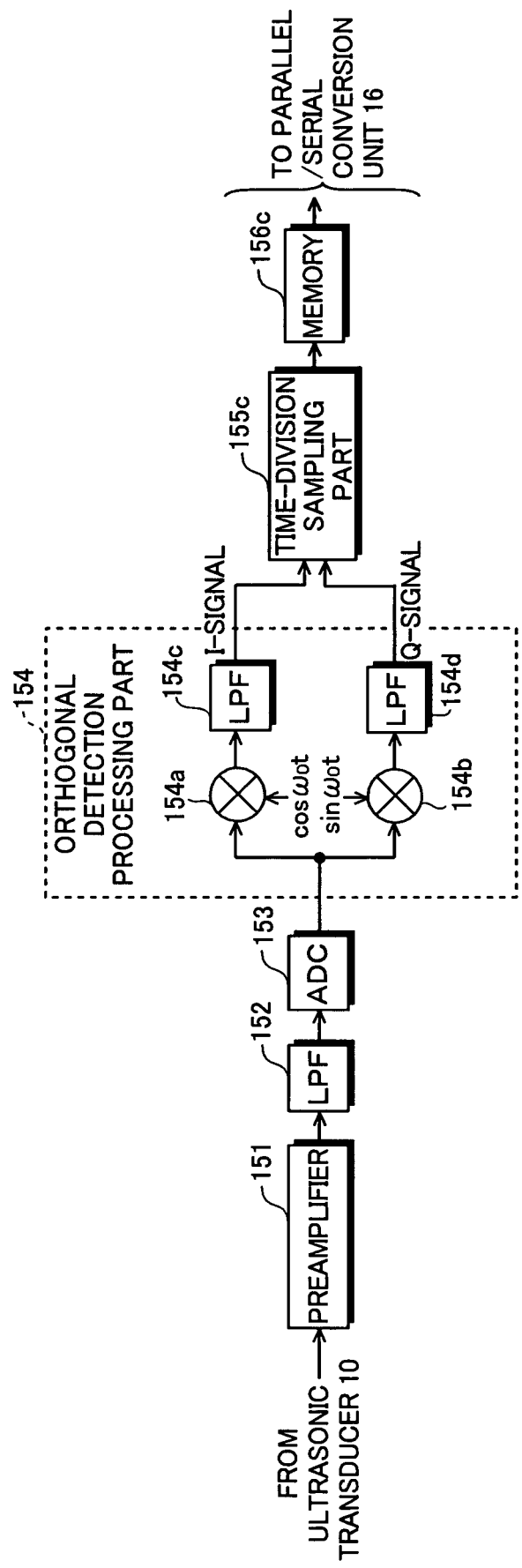

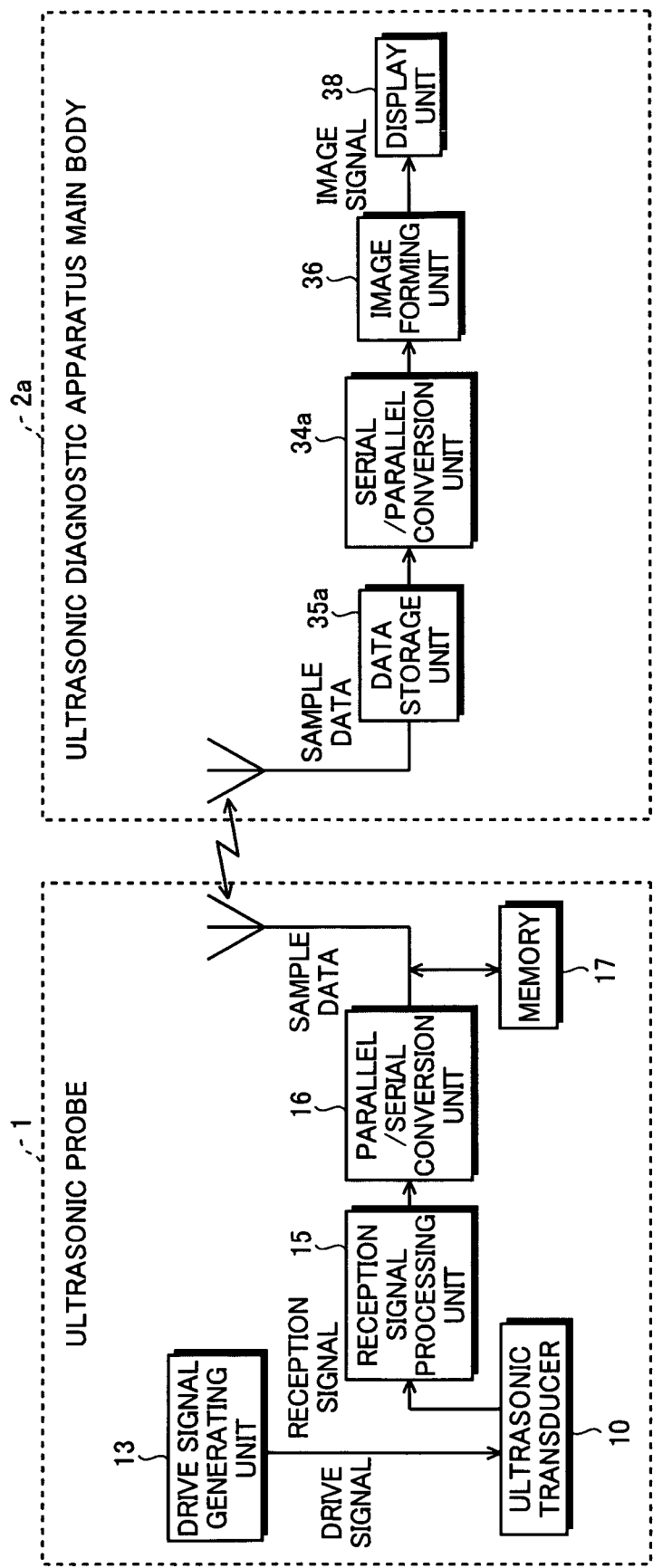

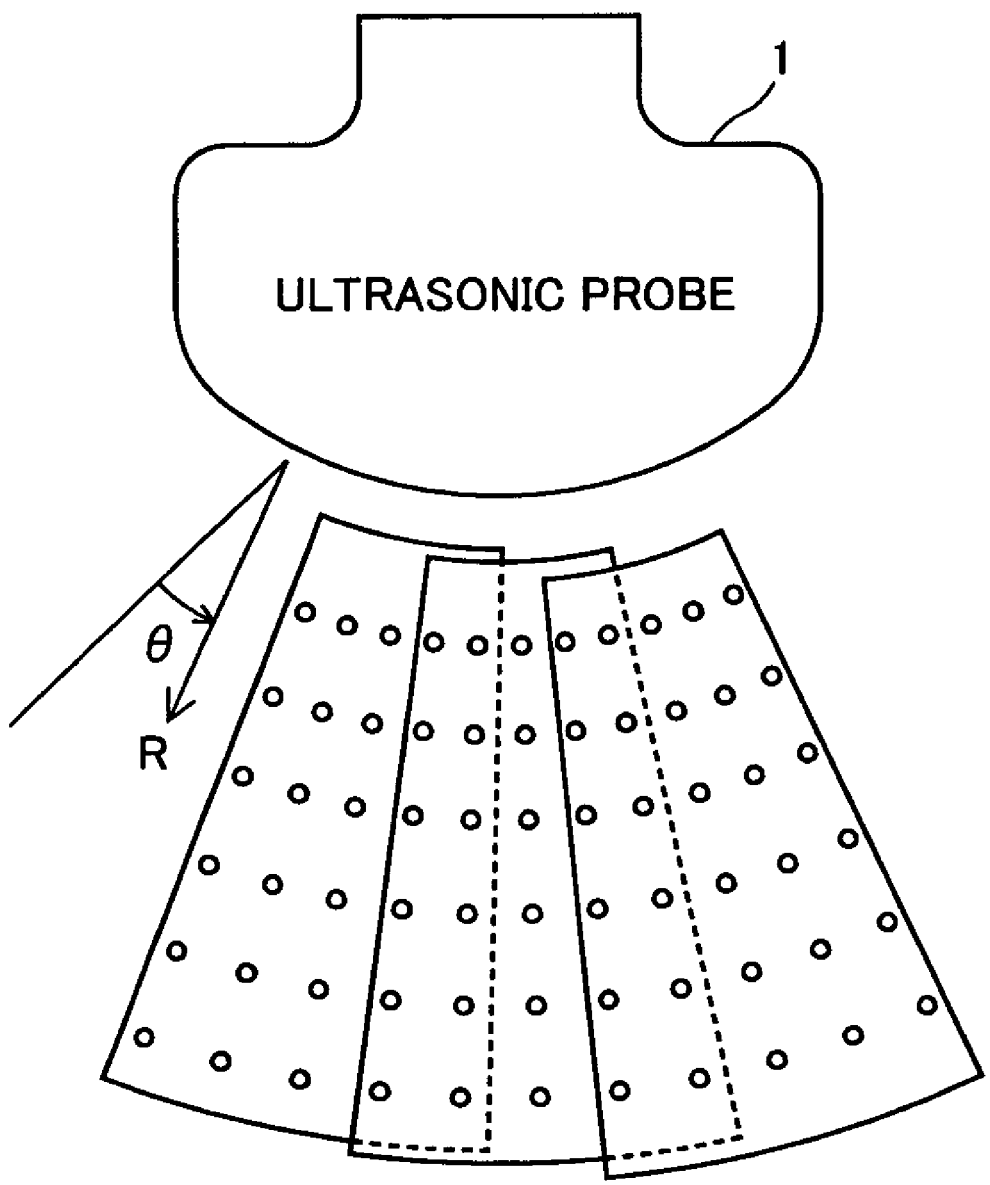

ULTRASONIC DIAGNOSTIC APPARATUS

CROSS-REFERENCE TO RELATED APPLICATION

The present application claims priority from Japanese Patent Applications No. 2009-097733 filed on Apr. 14, 2009 and No. 2009-101770 filed on Apr. 20, 2009, the contents of which are incorporated herein by reference in their entirety.

BACKGROUND OF THE INVENTION

1. Field of the Invention

The present invention relates to an ultrasonic diagnostic apparatus for imaging organs and so on within a living body by transmitting and receiving ultrasonic waves to generate ultrasonic diagnostic images to be used for diagnoses.

2. Description of a Related Art

In medical fields, various imaging technologies have been developed for observation and diagnoses within an object to be inspected. Especially, ultrasonic imaging for acquiring interior information on the object by transmitting and receiving ultrasonic waves enables image observation in real time and provides no exposure to radiation unlike other medical image technologies such as X-ray photography or RI (radio isotope) scintillation camera. Accordingly, ultrasonic imaging is utilized as an imaging technology at a high level of safety in a wide range of departments including not only the fetal diagnosis in obstetrics, but also gynecology, circulatory system, digestive system, and so on.

The principle of ultrasonic imaging is as follows. Ultrasonic waves are reflected at a boundary between regions having different acoustic impedances such as a boundary between structures within the object. Therefore, by transmitting ultrasonic beams into the object such as a human body, receiving ultrasonic echoes generated within the object, and obtaining reflection points where the ultrasonic echoes are generated and reflection intensity, outlines of structures (e.g., internal organs, diseased tissues, and so on) existing within the object can be extracted.

Generally, in an ultrasonic diagnostic apparatus, an ultrasonic probe including plural ultrasonic transducers (vibrators) having transmitting and receiving functions of ultrasonic waves is used. Reception signals outputted from the vibrators that have received ultrasonic echoes have delays according to differences of distances between the focus of ultrasonic waves and the respective vibrators. Accordingly, beam forming processing (reception focusing processing) of forming a focus in a specific position is performed by providing the delays according to the positions of the vibrators to those reception signals and adding those reception signals to one another. In this regard, until the reception signals are added to one another, those reception signals are treated as parallel data.

The reception focusing processing is typically performed by digital signal processing. That is, the A/D-converted reception signals are accumulated in a memory and read out while the readout times are changed as needed, and appropriately interpolated and added to one another. When the reception signals are added to one another, the number of channels of signals becomes single, and signal transfer can be performed by wireless communication. Therefore, by incorporating a circuit for performing reception focusing processing into the ultrasonic probe, the number of signal lines connecting between the ultrasonic probe and an ultrasonic diagnostic apparatus main body can be reduced, and further, wireless communication can be realized.

However, in the reception focusing processing, since amounts of delay to be provided to the reception signals vary depending on the position of the focus, control of the readout times from the memory is extremely complex and a large-scaled circuit is necessary. If such a circuit is incorporated into the ultrasonic probe, the probe size becomes not the practical size that can be operated with one hand. Further, since the ultrasonic diagnostic apparatus main body receives data after beam forming and sequentially generates images based on the data, when transfer quality is poor, there is a problem that a moving image cannot be generated smoothly due to reception delay of data with respect to a certain line or the like.

As a related technology, Japanese Patent Application Publication JP-P2003-299648A discloses an ultrasonic diagnostic apparatus having an ultrasonic probe by which a transfer cable can be made thinner and lighter even when the number of vibrating elements increases with higher definition, and maintenance and improvement of operability can be realized. The ultrasonic diagnostic apparatus includes an ultrasonic probe for performing transmission and reception of ultrasonic pulses for a living body by using plural vibrating elements, and an apparatus main body connected to the ultrasonic probe via a transfer cable, for generating transmission signals for transmitting ultrasonic pulses from the ultrasonic probe and forming an ultrasonic image from reception signals based on ultrasonic pulses (echoes) reflected by the living body and received by the ultrasonic probe. The ultrasonic diagnostic apparatus is characterized in that the transmission signals and reception signals transferred between the ultrasonic probe and the apparatus main body via the transfer cable are time-divisionally sectioned into chips for each vibrating element before transfer, and the respective chips are sequentially transferred by using a common signal line within the transfer cable.

However, in the ultrasonic diagnostic apparatus according to JP-P2003-299648A, the reception signals outputted from the respective vibrating elements are transferred in the unchanged frequency band, and therefore, the data volume cannot be reduced and a high transfer rate is necessary. Further, since the reception signals are time-divisionally transferred, there is no guarantee that the beam forming processing can be performed reliably after transfer.

Japanese Patent Application Publication JP-P2002-85405A discloses an ultrasonic diagnostic apparatus for the purpose of improvements in workability of ultrasonic examiners such as an improvement of operability of an ultrasonic probe. The ultrasonic diagnostic apparatus is constituted to be physically separable into (i) an ultrasonic collecting/operating unit having ultrasonic transducers, ultrasonic signal transmitting and receiving means for transmitting and receiving ultrasonic signals between an object to be inspected and itself via the ultrasonic transducers, ultrasonic beam forming means for generating ultrasonic beam data from output of the ultrasonic signal transmitting and receiving means, signal processing means for converting the ultrasonic beam data into data for generating image data, wireless communication means for transmitting the converted ultrasonic beam data as a wireless signal, and operating means for controlling ultrasonic signal collection, and (ii) an ultrasonic image generating and displaying unit having wireless receiving means for wirelessly receiving the ultrasonic beam data, image generating means for generating image data from the ultrasonic beam data, and image display means for displaying the image data.

However, in the ultrasonic diagnostic apparatus according to JP-P2002-85405A, the reception signals outputted from the plural ultrasonic transducers are serialized after beam forming, and therefore, a front-end circuit as a whole in a conventional ultrasonic diagnostic apparatus should be accommodated within the ultrasonic collecting/operating unit. Therefore, not only the circuit scale is huge but also a high transfer speed for serial communication is required.

Japanese Patent Application Publication JP-P2008-18107A discloses a wireless ultrasonic diagnostic apparatus for performing wireless transfer between an ultrasonic probe and an apparatus main body. In the ultrasonic diagnostic apparatus, the ultrasonic probe includes plural vibrators, amplifiers and A/D converters corresponding to the plural vibrators, a digital beam former, a PS conversion unit, a control data insertion unit, a modulator, and a power amplifier. In the ultrasonic probe, digital beam forming processing is performed to generate phase-matched and added data, and further, the phase-matched and added data is parallel/serial converted.

However, in the ultrasonic diagnostic apparatus according to JP-P2008-18107A, the reception signals outputted from the plural vibrators are serialized after beam forming, and therefore, a front-end circuit as a whole in a conventional ultrasonic diagnostic apparatus should be accommodated within the ultrasonic probe. Therefore, not only the circuit size is huge but also a high transfer speed for serial communication is required.

U.S. Pat. No. 6,251,073 B1 and U.S. Pat. No. 6,773,399 B2 disclose an ultrasonic diagnostic apparatus for generating an ultrasonic image without deteriorating the resolution while a width of an ultrasonic beam to be transmitted from an ultrasonic transducer array is broadened to make a broad beam. In U.S. Pat. No. 6,251,073 B1 and U.S. Pat. No. 6,773,399 B2, however, there is no disclosure as to reducing an amount of data within an ultrasonic probe when reception signals are transferred from the ultrasonic probe to an ultrasonic diagnostic apparatus main body.

SUMMARY OF THE INVENTION

The present invention has been achieved in view of the above-mentioned points. A first purpose of the present invention is, in an ultrasonic diagnostic apparatus for performing serial transfer between an ultrasonic probe and an ultrasonic diagnostic apparatus main body, to enable stable image formation even when transfer quality is poor while realizing downsizing or lower power consumption of the ultrasonic probe. A second purpose of the present invention is, in an ultrasonic diagnostic apparatus for performing serial transfer between an ultrasonic probe and an ultrasonic diagnostic apparatus main body, to improve transfer quality by reducing data volume in serial transfer while realizing downsizing or lower power consumption of the ultrasonic probe.

In order to accomplish the above-mentioned purposes, an ultrasonic diagnostic apparatus according to a first aspect of the present invention includes: (i) an ultrasonic probe including plural ultrasonic transducers for transmitting an ultrasonic beam according to drive signals and receiving ultrasonic echoes to output reception signals, reception signal processing means for generating parallel sample data based on the reception signals outputted from the plural ultrasonic transducers, parallel/serial conversion means for converting the parallel sample data generated by the reception signal processing means into serial sample data, and communication means for transmitting the sample data converted by the parallel/serial conversion means; and (ii) an ultrasonic diagnostic apparatus main body including storage means for storing the sample data of at least one frame transmitted from the ultrasonic probe, and image forming means for generating an image signal by performing reception focusing processing on the sample data with respect to every one frame read out from the storage means.

Further, an ultrasonic diagnostic apparatus according to a second aspect of the present invention includes: (i) an ultrasonic probe including plural ultrasonic transducers for transmitting a broad ultrasonic beam covering a tissue area within an object to be inspected according to drive signals and receiving ultrasonic echoes reflected from the tissue area within the object to output reception signals, reception signal processing means for generating parallel raw data including information on the tissue area based on the reception signals outputted from the plural ultrasonic transducers, parallel/serial conversion means for converting the parallel raw data generated by the reception signal processing means into serial raw data, and communication means for transmitting the raw data converted by the parallel/serial conversion means; and (ii) an ultrasonic diagnostic apparatus main body including image forming means for generating an image signal by performing reception focusing processing on the raw data transmitted from the ultrasonic probe.

According to the first aspect of the present invention, since reception focusing processing is not performed within the ultrasonic probe, downsizing or lower power consumption of the ultrasonic probe can be realized. Further, in the ultrasonic diagnostic apparatus main body, sample data of at least one frame is stored into the storage means and an image signal is generated based on the sample data with respect to every one frame read out from the storage means, and thereby, influences of image deficiency or transmission delay within one frame can be prevented. As a result, stable image formation can be performed even when transfer quality is poor.

Furthermore, according to the second aspect of the present invention, since reception focusing processing is not performed within the ultrasonic probe, downsizing or lower power consumption of the ultrasonic probe can be also realized. Further, an image signal is generated by using raw data obtained based on reception signals of ultrasonic echoes reflected from the tissue area within the object and including information on the tissue area, the number of transmissions and receptions of ultrasonic waves can be reduced. As a result, the data volume in serial transfer can be reduced and the transfer quality can be improved.

BRIEF DESCRIPTION OF THE DRAWINGS

FIG. 3 shows a first configuration example of a transmission signal processing unit as shown in FIG. 1;

FIG. 5 shows a second configuration example of the reception signal processing unit as shown in FIG. 1;

FIG. 11 is a block diagram showing parts of the configuration of the ultrasonic diagnostic apparatus according to a modified example of the first embodiment of the present invention;

FIG. 12C shows a modified example of the ultrasonic transmission and reception method;

DESCRIPTION OF THE PREFERRED EMBODIMENTS

Hereinafter, embodiments of the present invention will be explained in detail with reference to the drawings. The same characters are assigned to the same component elements and the explanation thereof will be omitted.

Figure 1:
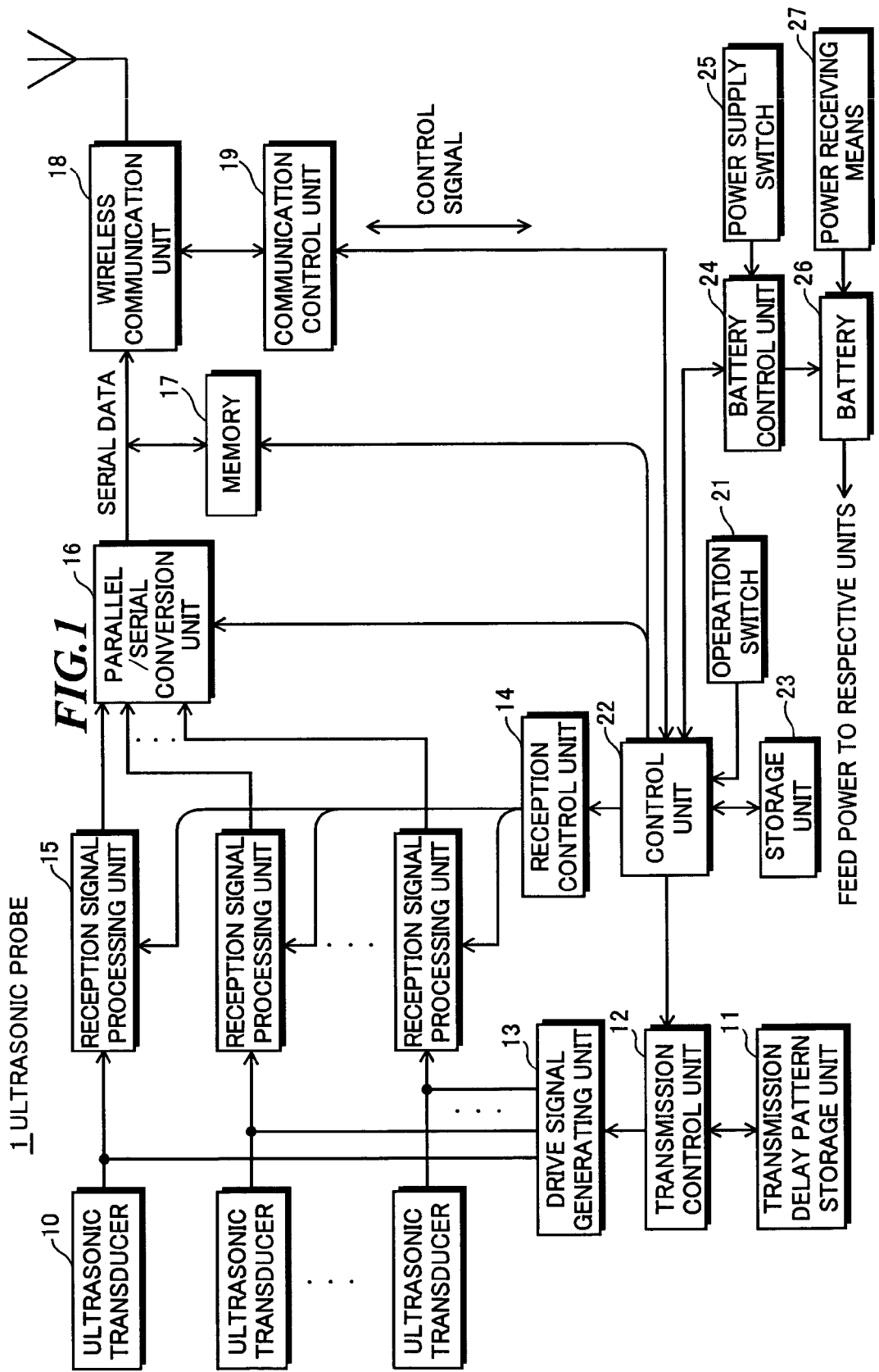
FIG. 1 is a block diagram showing a configuration of an ultrasonic probe in an ultrasonic diagnostic apparatus according to the first embodiment of the present invention.
Figure 2:
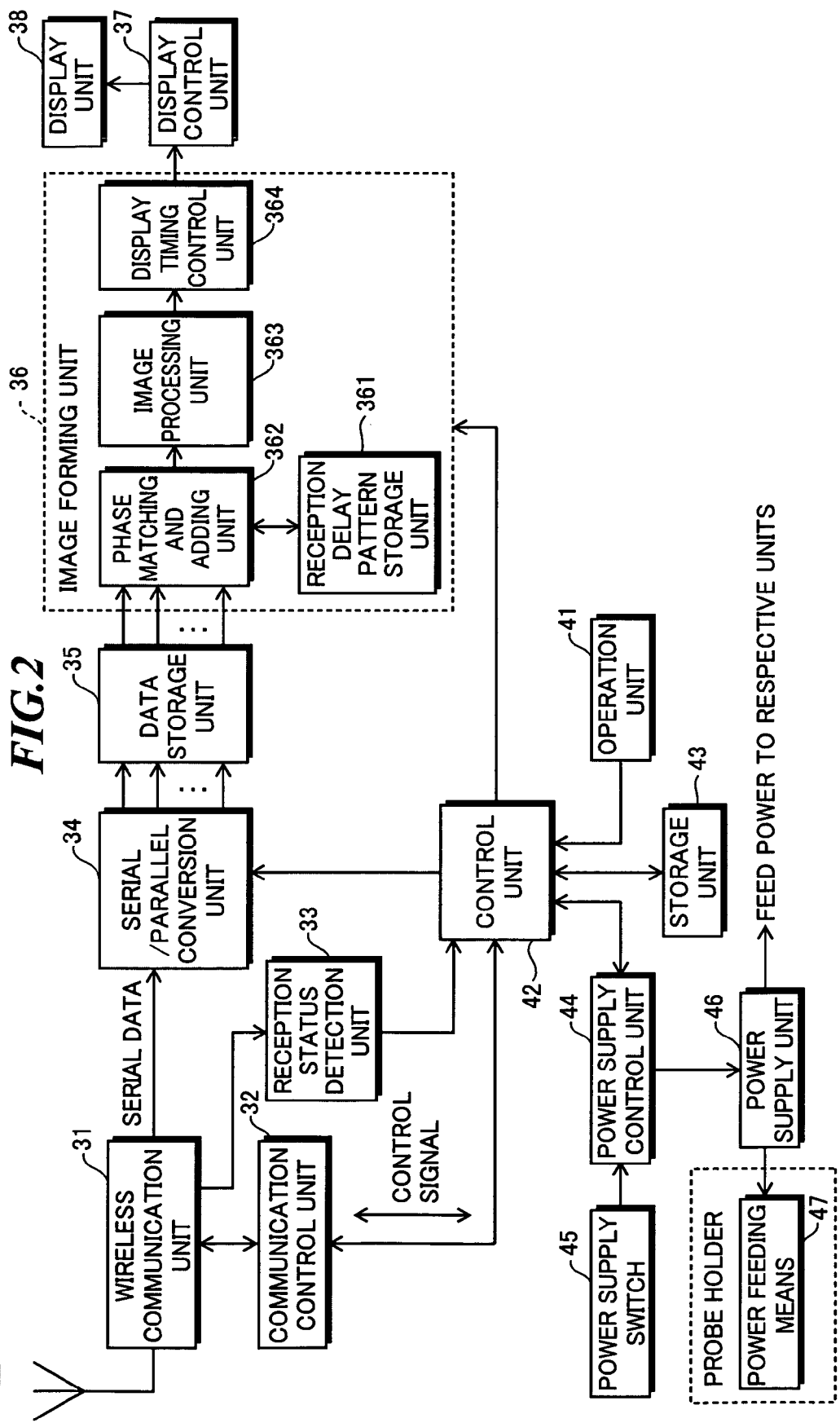
FIG. 2 is a block diagram showing a configuration of an ultrasonic diagnostic apparatus main body in the ultrasonic diagnostic apparatus according to the first embodiment of the present invention.

FIG. 1 is a block diagram showing a configuration of an ultrasonic probe in an ultrasonic diagnostic apparatus according to the first embodiment of the present invention, and FIG. 2 is a block diagram showing a configuration of an ultrasonic diagnostic apparatus main body in the ultrasonic diagnostic apparatus according to the first embodiment of the present invention. The ultrasonic diagnostic apparatus according to the first embodiment of the present invention includes an ultrasonic probe 1 as shown in FIG. 1 and the ultrasonic diagnostic apparatus main body as shown in FIG. 2. The ultrasonic probe 1 may be an external probe of linear-scan type, convex-scan type, sector-scan type, or the like, or an ultrasonic endoscopic probe of radial-scan type or the like.

As shown in FIG. 1, the ultrasonic probe 1 includes plural ultrasonic transducers 10 forming a one-dimensional or two-dimensional transducer array, a transmission delay pattern storage unit 11, a transmission control unit 12, a drive signal generating unit 13, a reception control unit 14, plural channels of reception signal processing units 15, a parallel/serial conversion unit 16, a memory 17, a wireless communication unit 18, a communication control unit 19, an operation switch 21, a control unit 22, a storage unit 23, a battery control unit 24, a power supply switch 25, a battery 26, and power receiving means 27. Here, the transmission delay pattern storage unit 11 to the drive signal generating unit 13 form drive signal generating means for generating drive signals to be supplied to the plural ultrasonic transducers 10.

The plural ultrasonic transducers 10 transmit ultrasonic waves according to applied drive signals and receive propagating ultrasonic echoes to output reception signals. Each ultrasonic transducer 10 includes a vibrator having electrodes formed on both ends of a material having a piezoelectric property (piezoelectric material) such as a piezoelectric ceramic represented by PZT (Pb (lead) zirconate titanate), a polymeric piezoelectric element represented by PVDF (polyvinylidene difluoride), or the like.

When a pulsed or continuous wave voltage is applied to the electrodes of the vibrator, the piezoelectric material expands and contracts. By the expansion and contraction, pulse or continuous wave ultrasonic waves are generated from the respective vibrators, and an ultrasonic beam is formed by synthesizing these ultrasonic waves. Further, the respective vibrators expand and contract by receiving the propagating ultrasonic waves to generate electric signals. These electric signals are outputted as reception signals of ultrasonic waves.

The transmission delay pattern storage unit 11 stores plural transmission delay patterns to be used when an ultrasonic beam is formed by using ultrasonic waves transmitted from the plural ultrasonic transducers 10. The transmission control unit 12 selects one transmission delay pattern from the plural transmission delay patterns stored in the transmission delay pattern storage unit 11 according to a transmission direction set by the control unit 22, and sets delay times to be respectively provided to the drive signals for the plural ultrasonic transducers 10 based on the selected transmission delay pattern.

The drive signal generating unit 13 includes plural pulsers as plural transmission circuits, for example, and adjusts the amounts of delay of the drive signals based on the transmission delay pattern selected by the transmission control unit 12 and supplies the drive signals to the plural ultrasonic transducers 10 such that the ultrasonic waves transmitted from the plural ultrasonic transducers 10 form an ultrasonic beam.

The reception control unit 14 controls the operation of the plural channels of reception signal processing units 15. Each channel of reception signal processing unit 15 performs orthogonal detection processing or orthogonal sampling processing on the reception signal outputted from the corresponding ultrasonic transducer 10 to generate a complex baseband signal, samples the complex baseband signal to generate sample data, and supplies the sample data to the parallel/serial conversion unit 16.

FIG. 3 shows a first configuration example of the reception signal processing unit as shown in FIG. 1. As shown in FIG. 3, each channel of reception signal processing unit 15 includes a preamplifier 151, a low-pass filter (LPF) 152, an analog/digital converter (ADC) 153, an orthogonal detection processing part 154, sampling parts 155a and 155b, and memories 156a and 156b. Here, the preamplifier 151 to the orthogonal detection processing part 154 form signal preprocessing means for performing orthogonal detection processing on the reception signal outputted from respective one of the plural ultrasonic transducers 10 to generate a complex baseband signal.

The preamplifier 151 amplifies the reception signal (RF signal) outputted from the ultrasonic transducer 10, and the LPF 152 limits a frequency band of the reception signal outputted from the preamplifier 151 to prevent aliasing in A/D conversion. The ADC 153 converts the analog reception signal outputted from the LPF 152 into a digital reception signal.

For example, when the frequency of ultrasonic waves is about 5 MHz, a sampling frequency of 40 MHz is used. In this case, the in vivo distance corresponding to one sample is about 0.038 mm, and data to the depth of about 15.7 cm is obtained with 4096 samples. Assuming that the number of ultrasonic transducers in the reception aperture is 64, and 100 ultrasonic reception lines (sound rays) are required for one frame of ultrasonic diagnostic image, data volume required for displaying one frame of image is $4096\times64\times100\approx26\times10^6$. Therefore, in order to display 10 frames of images per second, data transfer of about $260\times10^6$ pieces/sec is required. Since the resolving power necessary for an ultrasonic diagnostic image is generally about 12 bits for one piece of data, a transfer bit rate of about 3120 Mbps is required for transferring the above-mentioned data.

As described above, if serialization of data remaining in the RF signals is performed, the transfer bit rate becomes extremely higher, and the communication speed and the operation speed of the memories cannot keep up with the bit rate. On the other hand, as described in the explanation of the background art, if the data is serialized after reception focusing processing, the transfer bit rate can be reduced. However, a circuit for reception focusing processing is large-scaled and hard to be incorporated into the ultrasonic probe. Accordingly, in the embodiment, orthogonal detection processing or orthogonal sampling processing is performed on the reception signal to drop the frequency range of the reception signal to the baseband frequency range, and then, the data is serialized. Thereby, the transfer bit rate is reduced.

The orthogonal detection processing part 154 performs orthogonal detection processing on the reception signal to generate a complex baseband signal (I-signal and Q-signal). As shown in FIG. 3, the orthogonal detection processing part 154 includes mixers (multiplication circuits) 154a and 154b, and low-pass filters (LPFs) 154c and 154d. The mixer 154a multiplies the reception signal by a local oscillation signal $\cos\omega_0 t$, and the LPF 154c performs low-pass filter processing on the signal outputted from the mixer 154a, and thereby, an I-signal representing a real number component is generated. On the other hand, the mixer 154b multiplies the reception signal by a local oscillation signal $\sin\omega_0 t$, which is obtained by shifting the phase of the local oscillation signal $\cos\omega_0 t$ by $\pi/2$, and the LPF 154d performs low-pass filter processing on the signal outputted from the mixer 154b, and thereby, a Q-signal representing an imaginary number component is generated.

The sampling parts 155a and 155b sample (resample) the complex baseband signal (I-signal and Q-signal) generated by the orthogonal detection processing part 154, and thereby, generate two channels of sample data, respectively. The generated two channels of sample data are stored in the memories 156a and 156b, respectively.

Here, if the baseband signal is sampled at a frequency twice the baseband frequency range, signal information is held. Accordingly, the sampling frequency of 5 MHz is enough. Thereby, compared to the case where the data is serialized remaining in RF signals, the sampling frequency becomes lower from 40 MHz to 5 MHz, the data volume becomes ⅛, and the number of samples to the depth of about 15.7 cm becomes 512. Note that, in order to maintain the signal information by envelope detection, phase information should be held, and thus, it is necessary to generate the complex baseband signal (I-signal and Q-signal) by orthogonal detection processing or orthogonal sampling processing, and the number of channels of data becomes twice.

Therefore, the data volume necessary to display one frame of image is $512\times64\times100\times2\approx$ about $6.6\times10^6$, and in order to display 10 frames of images per second with resolving power of 12 bits, the transfer bit rate of about 792 Mbps is necessary. Further, if the sampling frequency is set to 2.5 MHz, the number of samples to the depth of about 15.7 cm is 256 and the data volume can be further reduced to the half, and thereby, the transfer bit rate may be about 396 MHz.

Figure 4A:
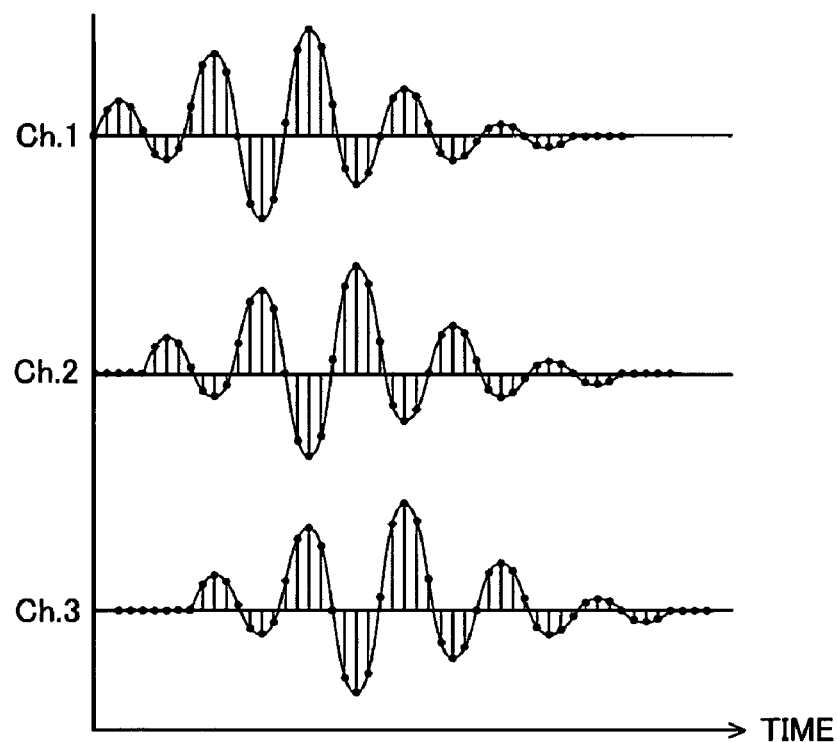
FIGS. 4A and 4B are waveform charts showing sampling by an ADC and sampling by a sampling part as shown in FIG. 3 in comparison.
Figure 4B:
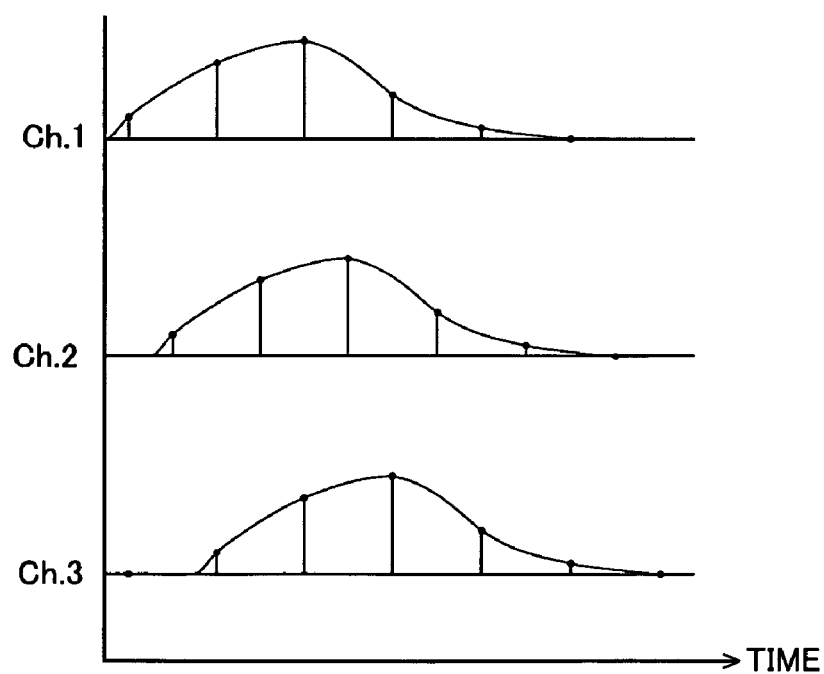

FIGS. 4A and 4B are waveform charts showing sampling by the ADC and sampling by the sampling part as shown in FIG. 3 in comparison. FIG. 4A shows sampling by the ADC 153 with respect to three channels Ch. 1 to Ch. 3, and FIG. 3B shows sampling by the sampling part 155a with respect to three channels Ch. 1 to Ch. 3. Compared to the case where the RF signals are sampled as shown in FIG. 4A and the sample data is transferred, the transfer bit rate can significantly be reduced by sampling the baseband signals as shown in FIG. 4B and transferring the sample data.

FIG. 5 shows a second configuration example of the reception signal processing unit as shown in FIG. 1. In the second configuration example as shown in FIG. 5, a time-division sampling part 155c is provided in place of the sampling parts 155a and 155b in the first configuration example as shown in FIG. 3, and a memory 156c is provided in place of the memories 156a and 156b.

The time-division sampling part 155c alternately and time-divisionally samples (resamples) the I-signal and the Q-signal generated by the orthogonal detection processing part 154, and thereby, generates two sequences of sample data. For example, the time-division sampling part 155c samples the I-signal in synchronization with the phase of the local oscillation signal $\cos\omega_0 t$, and samples the Q-signal in synchronization with the phase of the local oscillation signal $\sin\omega_0 t$. The generated two sequences of sample data are stored in the memory 156c. Thereby, the memory circuit can be provided in one route.

Figure 6:
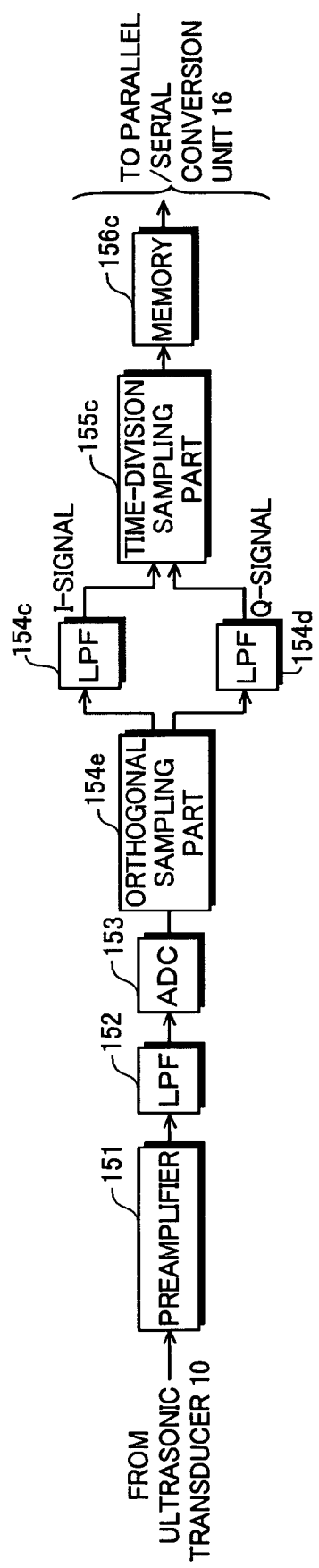
FIG. 6 shows a third configuration example of the reception signal processing unit as shown in FIG. 1.

FIG. 6 shows a third configuration example of the reception signal processing unit as shown in FIG. 1. In the third configuration example as shown in FIG. 6, an orthogonal sampling part 154e is provided in place of the mixers 154a and 154b in the second configuration example as shown in FIG. 5. Here, the preamplifier 151 to the LPFs 154c and 154d form signal preprocessing means for performing orthogonal sampling processing on the reception signal outputted from respective one of the plural ultrasonic transducers 10 to generate a complex baseband signal.

Figure 7:
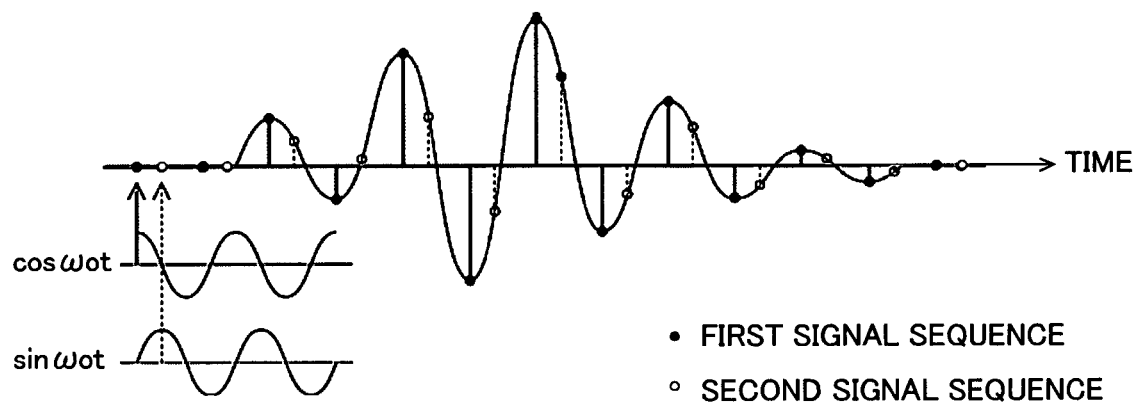
FIG. 7 is a waveform chart for explanation of an operation of an orthogonal sampling part as shown in FIG. 6.

FIG. 7 is a waveform chart for explanation of an operation of the orthogonal sampling part as shown in FIG. 6. The orthogonal sampling part 154e samples the reception signal, which has been converted into a digital signal by the ADC 153, in synchronization with the phase of the local oscillation signal $\cos\omega_0 t$ to generate a first signal sequence, and samples the reception signal in synchronization with the phase of the local oscillation signal $\sin\omega_0 t$ to generate a second signal sequence.

Further, the LPF 154c performs low-pass filter processing on the first signal sequence outputted from the orthogonal sampling part 154e, and thereby, an I-signal representing a real number component is generated. The LPF 154d performs low-pass filter processing on the second signal sequence outputted from the orthogonal sampling part 154e, and thereby, a Q-signal representing an imaginary number component is generated. Thereby, the mixers 154a and 154b as shown in FIG. 5 may be omitted.

Referring to FIG. 1 again, the parallel/serial conversion unit 16 converts the parallel sample data generated by the plural channels of reception signal processing units 15 into serial sample data. For example, the parallel/serial conversion unit 16 converts 128 channels of parallel data obtained based on the 64 reception signals outputted from the 64 ultrasonic transducers into one or more channel of serial sample data. Thereby, compared to the number of ultrasonic transducers, the number of transfer channels is significantly reduced. The memory 17 temporarily stores the serial sample data converted by the parallel/serial conversion unit 16.

The wireless communication unit 18 modulates a carrier based on the serial sample data to generate a transfer signal, and supplies the transfer signal to an antenna to transmit electric waves from the antenna, and thereby, transmits the serial sample data. As a modulation method, for example, ASK (amplitude shift keying), PSK (phase shift keying), QPSK (quadrature phase shift keying), 16 QAM (16 quadrature amplitude modulation), or the like is used. In the case of using ASK or PSk, one channel of serial data can be transferred in one route, in the case of using QPSK, two channels of serial data can be transferred in one route, and in the case of using 16 QAM, four channels of serial data can be transferred in one route.

The wireless communication unit 18 performs wireless communication between the ultrasonic diagnostic apparatus main body 2 (FIG. 2) and itself, and thereby, transmits the sample data to the ultrasonic diagnostic apparatus main body 2, and receives various kinds of control signals from the ultrasonic diagnostic apparatus main body 2 to output the received control signals to the communication control unit 19.

The communication control unit 19 controls the wireless communication unit 18 such that transmission of the sample data is performed with transmission electric wave intensity set by the control unit 22, and outputs the various kinds of control signals received by the wireless communication unit 18 to the control unit 22. The control unit 22 controls the respective units of the ultrasonic probe 1 according to the various kinds of control signals transmitted from the ultrasonic diagnostic apparatus main body 2.

The operation switch 21 includes a switch for setting the ultrasonic diagnostic apparatus in a live mode or a freeze mode. The setting signal for the live mode or the freeze mode is included in the transfer signal together with the sample data and transmitted to the ultrasonic diagnostic apparatus main body 2. Alternatively, the switching between the live mode and the freeze mode may be performed in the ultrasonic diagnostic apparatus main body 2.

The battery 26 supplies power to the respective units requiring power such as the drive signal generating unit 13 and the reception signal processing units 15. The ultrasonic probe 1 is provided with the power supply switch 25, and the battery control unit 24 controls whether the power is supplied from the battery 26 to the respective units or not according to the status of the power supply switch 25. The battery 26 can be charged by using the power receiving means 27.

In the above-mentioned configuration, the transmission control unit 12, the reception control unit 14, the orthogonal detection processing part 154 (FIG. 3), the sampling parts 155*a* and 155*b* (FIG. 3), the parallel/serial conversion unit 16, the communication control unit 19, the control unit 22, the battery control unit 24, and so on may be formed of digital circuits such as FPGAs (Field Programmable Gate Arrays), or formed of a central processing unit (CPU) and software (program) for allowing the CPU to perform various kinds of processing. The software (program) is stored in the storage unit 23.

In the case of using FPGAs as general-purpose circuits, even when the circuit scale is reduced, the number of contained electronic components is little affected. However, when the circuit scale becomes smaller, the capacity of the FPGA may be smaller and the smaller electronic components can be used, which has a great influence on the packaging area. Alternatively, the orthogonal detection processing part 154 may be formed of an analog circuit. In this case, the ADC 153 is omitted, and A/D conversion of the complex baseband signal is performed by the sampling parts 155*a* and 155*b*.

On the other hand, referring to FIG. 2, the ultrasonic diagnostic apparatus main body 2 includes a wireless communication unit 31, a communication control unit 32, a reception status detection unit 33, a serial/parallel conversion unit 34, a data storage unit 35, an image forming unit 36, a display control unit 37, a display unit 38, an operation unit 41, a control unit 42, a storage unit 43, a power supply control unit 44, a power supply switch 45, a power supply unit 46, and power feeding means 47.

The wireless communication unit 31 performs wireless communication between the ultrasonic probe 1 (FIG. 1) and itself, and thereby, transmits various kinds of control signals to the ultrasonic probe 1. Further, the wireless communication unit 31 demodulates the signal received by an antenna to output the serial sample data.

The communication control unit 32 controls the wireless communication unit 31 such that transmission of the various kinds of control signals is performed with transmission electric wave intensity set by the control unit 42. Further, the reception status detection unit 33 detects the reception status of the sample data transmitted from the ultrasonic probe 1, and outputs a detection result to the control unit 42. The detection of the reception status may be performed according to the level of the carrier received by the wireless communication unit 31. Alternatively, an error correction code may be added to the sample data by the wireless communication unit 18 of the ultrasonic probe 1 in advance, the wireless communication unit 31 may perform error detection and error correction of the sample data, and the reception status detection unit 33 may detect the reception status based on an error rate obtained in the wireless communication unit 31.

The control unit 42 controls the wireless communication unit 31 via the communication control unit 32 to transmit a retransmission request to the ultrasonic probe 1 when the reception status detected by the reception status detection unit 33 is not better than a predetermined level. The control unit 22 of the ultrasonic probe 1 as shown in FIG. 1 allows the wireless communication unit 18 to transmit the sample data read out from the memory 17 in response to the retransmission request from the ultrasonic diagnostic apparatus main body 2. Thereby, an ultrasonic diagnostic image can be displayed without error even when transfer quality is poor.

The serial/parallel conversion unit 34 converts the serial sample data outputted from the wireless communication unit 31 into 128 channels of parallel sample data representing 64 complex baseband signals obtained based on the reception signals outputted from the 64 ultrasonic transducers, for example. The data storage unit 35 is formed of a memory, hard disk, or the like, and stores sample data of at least one frame converted by the serial/parallel conversion unit 34.

The image forming unit 36 generates an image signal representing an ultrasonic diagnostic image by performing reception focusing processing on the sample data with respect to every one frame read out from the data storage unit 35. In this manner, by acquiring sample data with respect to every one frame and then generating an image signal to display a moving image, influences of image deficiency or transmission delay within one frame can be prevented. The image forming unit 36 includes a reception delay pattern storage unit 361, a phase matching and adding unit 362, an image processing unit 363, and a display timing control unit 364.

The reception delay pattern storage unit 361 stores plural reception delay patterns to be used when reception focusing processing is performed. The phase matching and adding unit 362 selects one reception delay pattern from the plural reception delay patterns stored in the reception delay pattern storage unit 361 according to the reception direction set in the control unit 42, and performs reception focusing processing by providing respective delays to the plural complex baseband signals represented by the sample data based on the selected reception delay pattern and adding the plural complex baseband signals to one another. By the reception focusing processing, baseband signals (sound ray signals) in which the focus of the ultrasonic echoes is narrowed are formed.

The image processing unit 363 generates B-mode image signals as tomographic image information on tissues within the object based on the sound ray signals generated by the phase matching and adding unit 362. The image processing unit 363 includes an STC (sensitivity time control) part, and a DSC (digital scan converter). The STC part performs attenuation correction by distance according to the depths of the reflection positions of ultrasonic waves on the sound ray signals. The DSC converts (raster-converts) the sound ray signals corrected by the STC part into an image signal that follows the scan system of general television signals, and performs necessary image processing such as gradation processing, and thereby, generates the B-mode image signal.

The display timing control unit 364 controls the timing when the image signal generated by the image processing unit 363 with respect to every one frame to the display control unit 37 such that an ultrasonic diagnostic image is displayed at an appropriate frame rate. The display control unit 37 allows the display unit 38 to display the ultrasonic diagnostic image based on the image signal generated by the image forming unit 34. The display unit 38 includes a display device such as an LCD, and displays the ultrasonic diagnostic image under the control of the display control unit 37.

The control unit 42 controls the respective units of the ultrasonic diagnostic apparatus according to the operation of an operator using the operation unit 41. The ultrasonic diagnostic apparatus main body 2 is provided with the power supply switch 45, and the power supply control unit 44 controls ON/OFF of the power supply unit 46 according to the status of the power supply switch 45. The power feeding means 47 provided in a probe holder feeds power to the power receiving means 27 (FIG. 1) of the ultrasonic probe 1 by the electromagnetic induction action.

In the above-mentioned configuration, the communication control unit 32, the serial/parallel conversion unit 34, the image forming unit 36, the display control unit 37, the control unit 42, and the power supply control unit 44 are formed of a control processing unit (CPU) and software (program) for allowing the CPU to perform various kinds of processing, but they may be formed of digital circuits. The software (program) is stored in the storage unit 43. As a recording medium in the storage unit 43, not only a built-in hard disk but also a flexible disk, MO, MT, RAM, CD-ROM, DVD-ROM, or the like may be used.

Figure 8A:
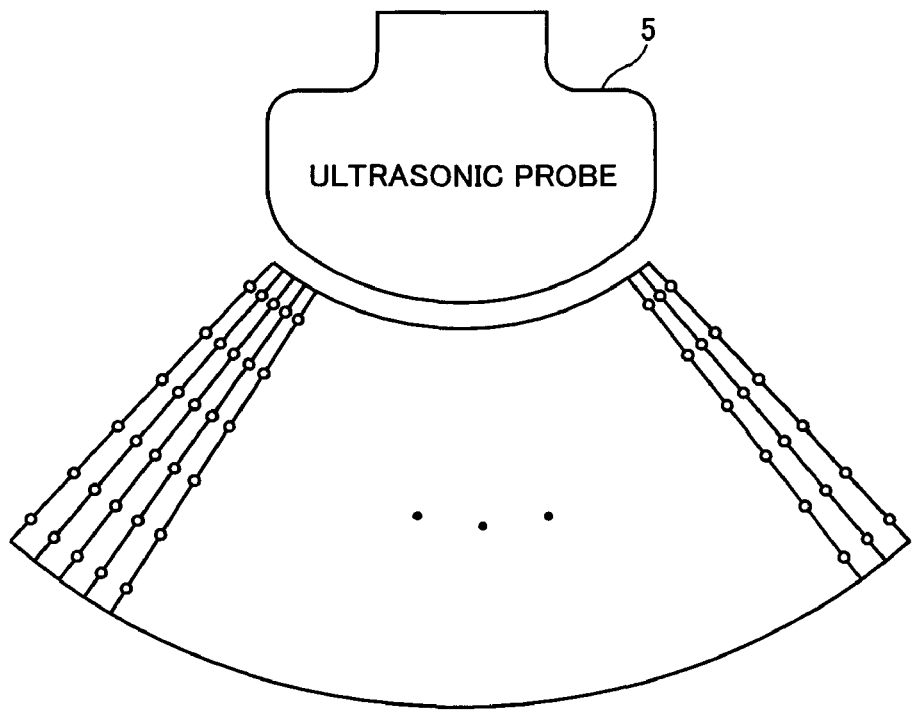
FIG. 8A shows a conventional ultrasonic transmission and reception method.

FIG. 8A shows a conventional ultrasonic transmission and reception method. In the ultrasonic transmission and reception method as shown in FIG. 8A, an ultrasonic beam along one line is transmitted from plural ultrasonic transducers (also simply referred to as "elements") included in an ultrasonic probe 5, and reception signals of ultrasonic echoes reflected from the object are sampled at plural sampling points on the line.

By repeating transmission and reception of ultrasonic waves while changing the direction of the line, reception signals for one frame are obtained. In one frame period, the number of transmissions of ultrasonic beams is equal to the number of lines, and the number of receptions of ultrasonic echoes is equal to a product of the number of lines and the number of sampling points on each line. In this example, 128 elements are used, and 256 transmissions are performed per one frame while shifting the elements to be used for transmitting ultrasonic waves by 0.5 elements. Further, the number of receiving elements to be used at one reception is set to 64, for example. The number of reception signals for one frame is a product of the number of receptions and the number of receiving elements.

Figure 8B:
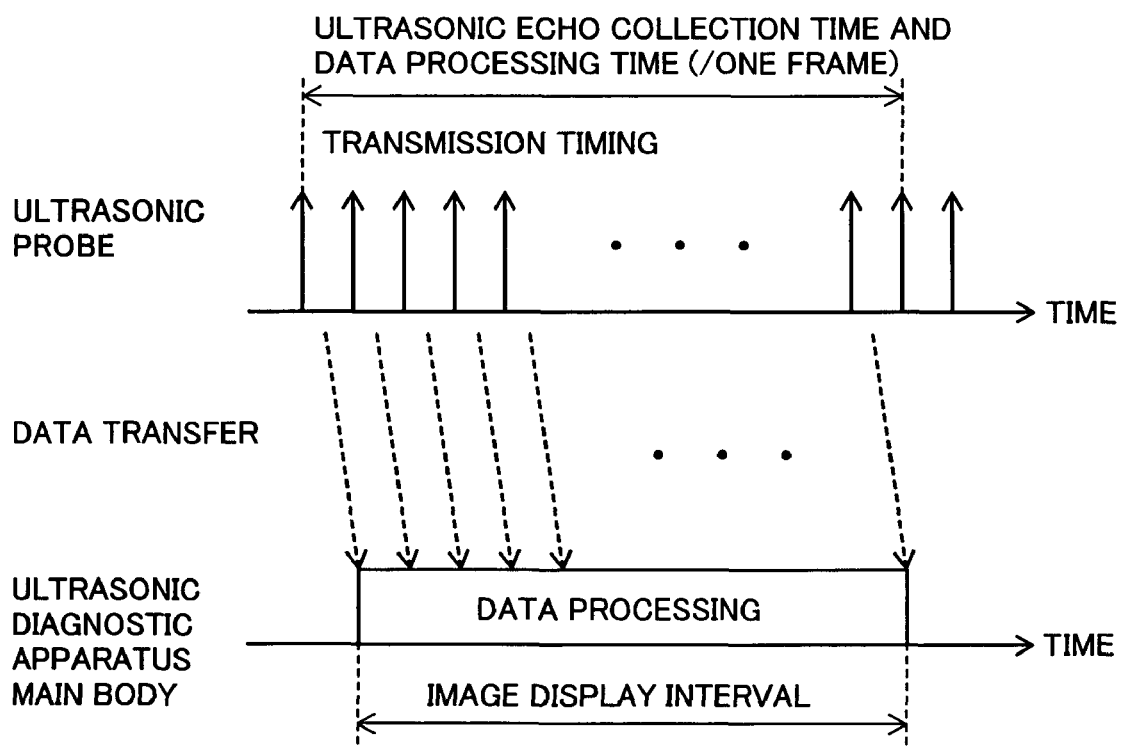
FIG. 8B is a timing chart showing transmission timing and data processing in the conventional ultrasonic transmission and reception method.

FIG. 8B is a timing chart showing transmission timing and data processing in the conventional ultrasonic transmission and reception method. When imaging is performed to a region at a depth of 15 cm, the time required from transmission of one ultrasonic beam to reception of the ultrasonic echo is 0.2 msec at a maximum, and therefore, the one frame period (image display interval) becomes 51.2 msec equal to the time for receiving the ultrasonic echoes for one frame, and the image display rate becomes 19.5 frame/sec.

In one frame period, ultrasonic beams are sequentially transmitted from the ultrasonic probe in 256 directions at 0.2 msec intervals, and line data is generated based on reception signals obtained by receiving ultrasonic echoes. The generated line data is transferred from the ultrasonic probe to an ultrasonic diagnostic apparatus main body, and processed in the ultrasonic diagnostic apparatus main body to generate an image signal.

Figure 9:
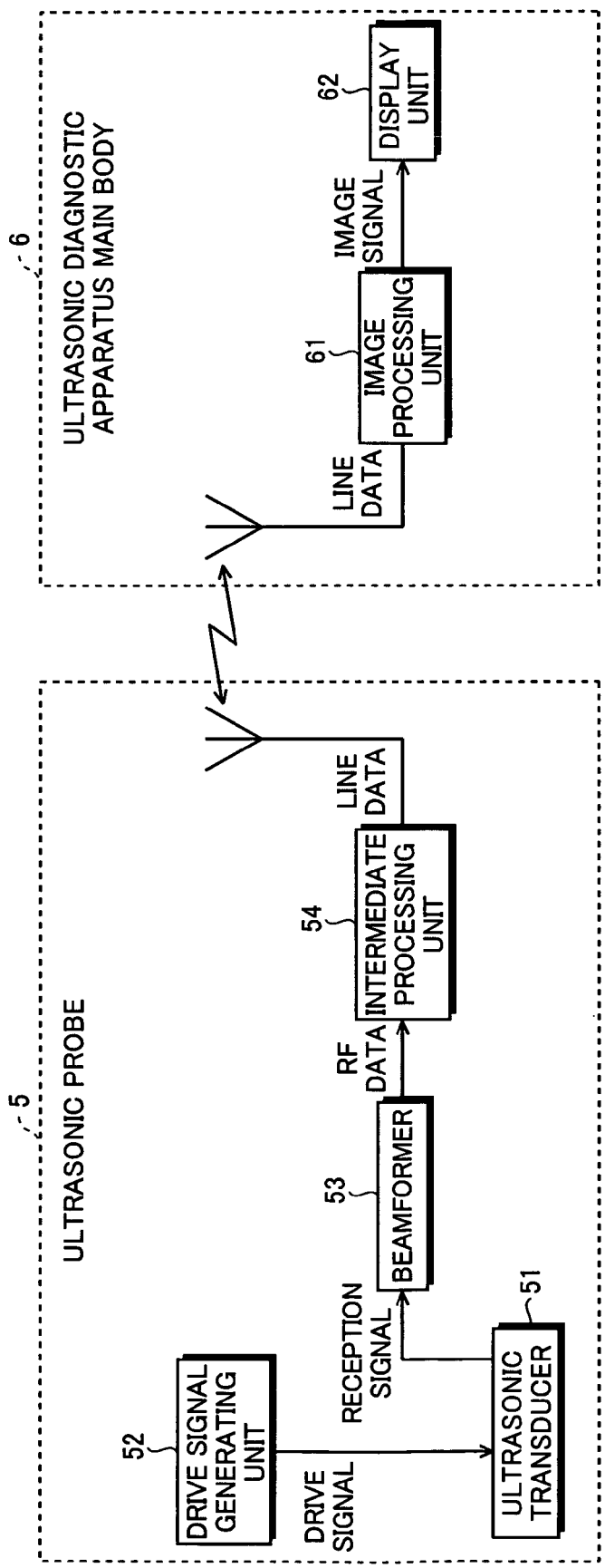
FIG. 9 is a block diagram showing a configuration example of an ultrasonic diagnostic apparatus for performing the conventional ultrasonic transmission and reception method.

FIG. 9 is a block diagram showing a configuration example of an ultrasonic diagnostic apparatus for performing the conventional ultrasonic transmission and reception method. The ultrasonic diagnostic apparatus includes the ultrasonic probe 5 and the ultrasonic diagnostic apparatus main body 6. The ultrasonic probe 5 includes plural ultrasonic transducers 51, a drive signal generating unit 52 for supplying drive signals to the plural ultrasonic transducers 51, a beamformer 53 for performing reception focusing processing on the reception signals outputted from the plural ultrasonic transducers 51 to generate RF data, an intermediate processing unit 54 for performing envelope detection processing on the RF data to generate line data and transmitting the generated line data to the ultrasonic diagnostic apparatus main body 6. The ultrasonic diagnostic apparatus main body 6 includes an image processing unit 61 for generating an image signal based on the line data received from the ultrasonic probe 5, and a display unit 62 for displaying an ultrasonic diagnostic image based on the image signal.

In the conventional ultrasonic transmission and reception method, the ultrasonic echo collection time per frame is equal to the image display interval, and therefore, even when an error occurs in transfer of the line data, there is no spare time to retransfer the line data or the like. As described above, the display rate of an ultrasonic diagnostic image in the display unit 62 is determined by the ultrasonic echo collection time. Accordingly, in the case where the communication condition between the ultrasonic probe 5 and the ultrasonic diagnostic apparatus main body 6 is poor and communication takes time, image display within one frame may be temporarily stopped at a certain line when the acquisition time of line data is temporarily delayed in the ultrasonic diagnostic apparatus main body 6, and further, moving image display cannot be performed at a fixed frame rate when the display frame rate is also affected, and unnatural moving image may be reproduced in which the frame rate temporarily changes.

Figure 10:
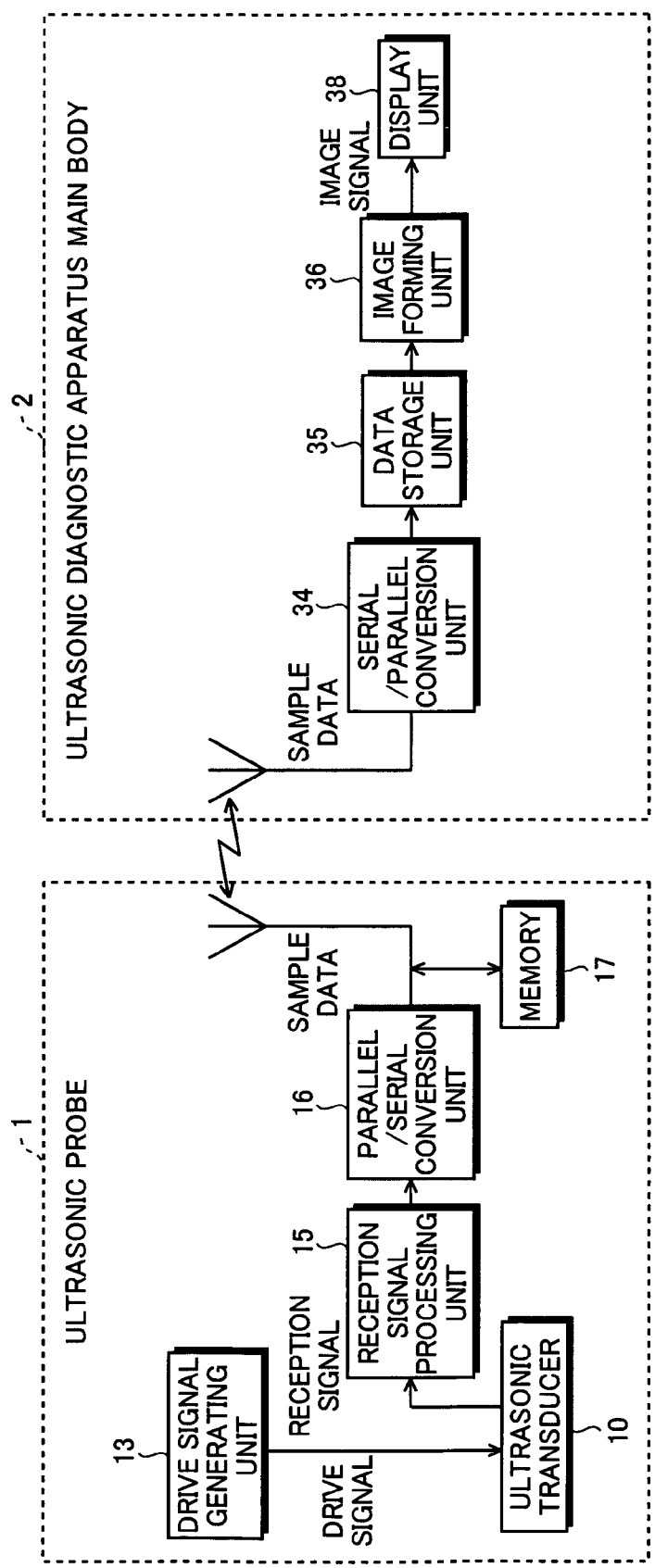
FIG. 10 is a block diagram showing parts of the configuration of the ultrasonic diagnostic apparatus according to the first embodiment of the present invention.

FIG. 10 is a block diagram showing parts of the configuration of the ultrasonic diagnostic apparatus according to the first embodiment of the present invention. In FIG. 10, the parts of the component elements of the ultrasonic diagnostic apparatus as shown in FIGS. 1 and 2 are extracted and shown. As shown in FIG. 10, the data storage unit 35 for storing sample data of at least one frame, and the image forming unit 36 for generating an image signal by performing reception focusing processing on the sample data with respect to every one frame read out from the data storage unit 35 are provided in the ultrasonic diagnostic apparatus main body 2. Thereby, image display can be performed at a fixed frame rate. Further, when the transfer quality between the ultrasonic probe 1 and the ultrasonic diagnostic apparatus main body 2 is poor, retransfer of the sample data becomes easier.

In the first embodiment, the sample data of at least one frame obtained based on the reception signals outputted from the plural ultrasonic transducers 10 is stored in the data storage unit 35 of the ultrasonic diagnostic apparatus main body 2, and then, the image forming unit 36 generates the image signal based on the sample data stored in the data storage unit 35 to display an ultrasonic diagnostic image on the display unit 38. Therefore, the display timing can freely be determined at the ultrasonic diagnostic apparatus main body 2 side.

Further, communication processing of the sample data and image signal generation processing based on the sample data are independently performed with respect to each frame. Therefore, complex control operation such as synchronization control of the communication processing and the image signal generation processing with respect to each line becomes no longer necessary, and a wireless system can be realized by simple circuit configuration and control operation.

Furthermore, when an error occurs in transfer of the sample data, the sample data can be retransferred from the ultrasonic probe 1 to the ultrasonic diagnostic apparatus main body 2 by transmitting a retransfer request from the ultrasonic diagnostic apparatus main body 2 to the ultrasonic probe 1.

According to the first embodiment, by storing the sample data of at least one frame in the data storage unit 35 and then generating the image signal based on the sample data with respect to every one frame read out from the data storage unit 35, influences of image deficiency or transmission delay within one frame can be prevented, and stable image formation can be performed even when transfer quality is poor.

In the first embodiment, the configuration is explained in which the data storage unit 35 is provided at a subsequent stage of the serial/parallel conversion unit 34 as shown in FIG. 10, and thereby, the data storage unit 35 stores the parallel sample data. However, the configuration as shown in FIG. 11 may be adopted in which a storage unit 35*a* is provided at a former stage of a serial/parallel conversion unit 34*a*, and thereby, the storage unit 35*a* stores the serial sample data.

According to the configuration as shown in FIG. 11, in the case where retransfer of the sample data is necessary because the transfer quality between the ultrasonic probe 1 and an ultrasonic diagnostic apparatus main body 2*a* becomes poor, the sample data transferred under the poor transfer quality and stored in the storage unit 35*a* can be erased and the retransfer processing of the sample data can be started without waiting for completion of the serial/parallel conversion processing.

Next, the second embodiment of the present invention will be explained. In the second embodiment, an image signal is generated by using raw data including information on a tissue area within the object obtained based on reception signals of ultrasonic echoes reflected from the tissue area. Thereby, the number of transmissions and receptions of ultrasonic waves is reduced, the data volume in serial transfer is reduced, and the transfer quality is improved. Further, the signal processing in the first embodiment for generating the image signal based on sample data with respect to every one frame may be combined. Since the configuration according to the second embodiment is nearly the same as the configuration according to the first embodiment that has been explained with reference to FIGS. 1-10, some drawings of FIGS. 1-10 will be referred to.

Referring to FIG. 1, the transmission delay pattern storage unit 11 stores plural transmission delay patterns to be used when an ultrasonic beam is formed by using ultrasonic waves transmitted from the plural ultrasonic transducers 10. The transmission control unit 12 selects one transmission delay pattern from the plural transmission delay patterns stored in the transmission delay pattern storage unit 11 according to a transmission direction set in the control unit 22, and sets delay times to be respectively provided to the drive signals for the plural ultrasonic transducers 10 based on the selected transmission delay pattern.

The drive signal generating unit 13 adjusts the amounts of delay of the drive signals and supplies the drive signals to the plural ultrasonic transducers 10 such that the ultrasonic waves transmitted from the plural ultrasonic transducers 10 form a broad ultrasonic beam that covers the tissue area within the object based on the transmission delay pattern selected by the transmission control unit 12.

Here, by setting the width of the ultrasonic beam broader than usual, one ultrasonic beam can cover one area not one line. It is desirable that the drive signal generating unit 13 generates the drive signals such that adjacent two areas covered by ultrasonic beams sequentially transmitted from the plural ultrasonic transducers 10 overlap with each other. By using such a broad ultrasonic beam, the number of transmissions and receptions of ultrasonic waves can be reduced.

The reception control unit 14 controls the operation of the plural channels of reception signal processing units 15. Each channel of reception signal processing unit 15 performs orthogonal detection processing or orthogonal sampling processing on the reception signal outputted from the corresponding ultrasonic transducer 10 to generate a complex baseband signal, samples the complex baseband signal to generate raw data including information on the tissue area, and supplies the raw data to the parallel/serial conversion unit 16. Further, the reception signal processing unit 15 may generate raw data by performing data compression processing for high-efficiency coding on data obtained by sampling the complex baseband signal. As the data compression processing, run-length compression, Huffman coding, or the like may be used.

The parallel/serial conversion unit 16 converts the parallel raw data generated by the plural channels of reception signal processing units 15 into serial raw data. The wireless communication unit 18 modulates a carrier based on the serial raw data to generate a transfer signal, and supplies the transfer signal to an antenna to transmit electric waves from the antenna, and thereby, transmits the serial raw data.

The wireless communication unit 18 performs wireless communication between the ultrasonic diagnostic apparatus main body 2 (FIG. 2) and itself, and thereby, transmits the raw data to the ultrasonic diagnostic apparatus main body 2, and receives various kinds of control signals from the ultrasonic diagnostic apparatus main body 2 to output the received control signals to the communication control unit 19.

The communication control unit 19 controls the wireless communication unit 18 such that transmission of the raw data is performed with transmission electric wave intensity set by the control unit 22, and outputs the various kinds of control signals received by the wireless communication unit 18 to the control unit 22. The control unit 22 controls the respective units of the ultrasonic probe 1 according to the various kinds of control signals transmitted from the ultrasonic diagnostic apparatus main body 2.

On the other hand, referring to FIG. 2, the wireless communication unit 31 performs wireless communication between the ultrasonic probe 1 (FIG. 1) and itself, and thereby, transmits various kinds of control signals to the ultrasonic probe 1. Further, the wireless communication unit 31 demodulates the signals received by an antenna to output the serial raw data.

The communication control unit 32 controls the wireless communication unit 31 such that transmission of the various kinds of control signals is performed with transmission electric wave intensity set by the control unit 42. Further, the reception status detection unit 33 detects the reception status of the raw data transmitted from the ultrasonic probe 1, and outputs a detection result to the control unit 42. The detection of the reception status may be performed according to the level of the carrier received by the wireless communication unit 31. Alternatively, an error correction code may be added to the raw data by the wireless communication unit 18 of the ultrasonic probe 1, the wireless communication unit 31 may perform error detection and error correction of the raw data, and the reception status detection unit 33 may detect the reception status based on an error rate obtained in the wireless communication unit 31.

The control unit 42 may control the wireless communication unit 31 via the communication control unit 32 to transmit a retransmission request to the ultrasonic probe 1 when the reception status detected by the reception status detection unit 33 is not better than a predetermined level. In this case, the control unit 22 of the ultrasonic probe 1 as shown in FIG. 1 allows the wireless communication unit 18 to transmit the raw data read out from the memory 17 in response to the retransmission request from the ultrasonic diagnostic apparatus main body 2. Thereby, an ultrasonic diagnostic image can be displayed without error even when transfer quality is poor.

The serial/parallel conversion unit 34 converts the serial raw data outputted from the wireless communication unit 31 into 128 channels of parallel raw data representing 64 complex baseband signals obtained based on the reception signals outputted from the 64 ultrasonic transducers, for example. The data storage unit 35 is formed of a memory, hard disk, or the like, and stores the raw data converted by the serial/parallel conversion unit 34. In the case where the signal processing in the first embodiment for generating an image signal based on sample data with respect to every one frame is adopted, the data storage unit 35 stores raw data of at least one frame.

The image forming unit 36 includes a reception delay pattern storage unit 361, a phase matching and adding unit 362, and an image processing unit 363, and generates an image signal representing an ultrasonic diagnostic image by performing reception focusing processing on the raw data read out from the data storage unit 35. In the case where the signal processing in the first embodiment is adopted, the image forming unit 36 further includes a display timing control unit 364, and generates the image signal representing the ultrasonic diagnostic image by performing reception focusing processing on the raw data with respect to every one frame read out from the data storage unit 35. In this manner, by acquiring the raw data with respect to every one frame, and then generating the image signal to display a moving image, influences of image deficiency or transmission delay within one frame can be prevented.

Figure 12A:
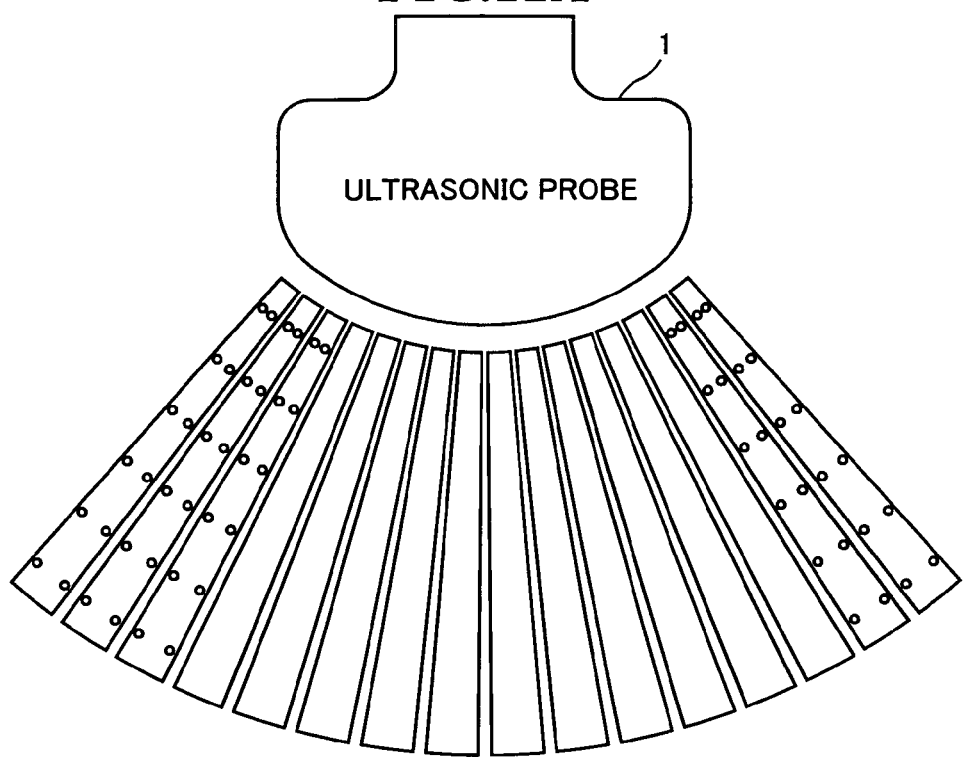
FIG. 12A shows an ultrasonic transmission and reception method used in an ultrasonic diagnostic apparatus according to the second embodiment of the present invention.

FIG. 12A shows an ultrasonic transmission and reception method used in the ultrasonic diagnostic apparatus according to the second embodiment of the present invention. In the ultrasonic transmission and reception method as shown in FIG. 12A, the width of the ultrasonic beam is set broader than usual, and thereby, a broad ultrasonic beam covering the tissue area within the object is transmitted from the plural ultrasonic transducers included in the ultrasonic probe 1, and reception signals of ultrasonic echoes reflected from the tissue area within the object are sampled at plural sampling points within the tissue area. Thus, area forming is performed. In the present application, the width of the ultrasonic beam is defined by a region in which sound pressure equal to or more than 90% of the peak sound pressure in front of the ultrasonic beam is obtained on a line orthogonal to the traveling direction of the ultrasonic beam.

By repeating transmission and reception of ultrasonic waves while changing the direction of the area, reception signals for one frame are obtained. In one frame period, the number of transmissions of ultrasonic beams is equal to the number of areas, and the number of receptions of ultrasonic echoes is equal to a product of the number of areas and the number of sampling points on a radius. In this example, 128 ultrasonic transducers are used, and 16 transmissions are performed per one frame while shifting the elements to be used for transmitting ultrasonic waves by 8 elements. Further, the number of receiving elements to be used at one reception is set to 64, for example. The number of reception signals for one frame is a product of the number of receptions and the number of receiving elements. It is desirable that the number of transmissions of ultrasonic beams is within a range from 16 to 64.

Figure 12B:
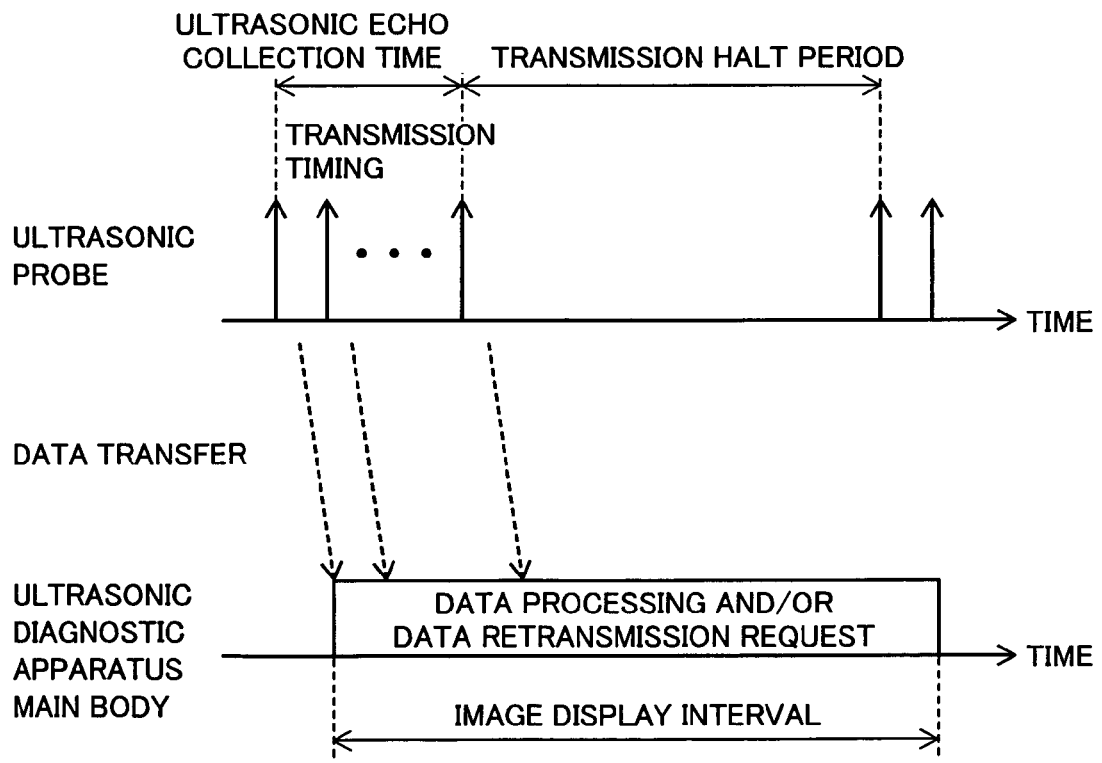
FIG. 12B is a timing chart showing transmission timing and data processing in the ultrasonic transmission and reception method.

FIG. 12B is a timing chart showing transmission timing and data processing in the ultrasonic transmission and reception method used in the ultrasonic diagnostic apparatus according to the second embodiment of the present invention. In the case where imaging is performed to a region at a depth of 15 cm, the time required from transmission of one ultrasonic beam to reception of the ultrasonic echo is 0.2 msec at a maximum. Here, similarly to the conventional ultrasonic transmission and reception method, one frame period (image display interval) is set to 51.2 msec and the image display rate is set to 19.5 frame/sec.

In one frame period, ultrasonic beams are sequentially transmitted from the ultrasonic probe in 16 directions (toward 16 areas) at 0.2 msec intervals, and raw data is generated based on reception signals obtained by reception of ultrasonic echoes. Since the time required for transmission and reception of ultrasonic waves per one frame is 3.2 msec, transmission of ultrasonic waves can be halted for 48 msec within the one frame period (51.2 msec). The generated raw data is transferred from the ultrasonic probe to an ultrasonic diagnostic apparatus main body, and processed in the ultrasonic diagnostic apparatus main body, and thereby, an image signal is generated.

According to the second embodiment, area forming is performed by using a broad ultrasonic beam, and thereby, the number of transmissions and receptions of ultrasonic waves can be reduced, and the data volume transmitted from the ultrasonic probe 1 to the ultrasonic diagnostic apparatus main body 2 can be reduced. Therefore, by reducing the transfer bit rate, transfer quality can be improved. Further, when the transfer quality between the ultrasonic probe 1 and the ultrasonic diagnostic apparatus main body 2 is poor, retransfer of the raw data becomes easier.

In the ultrasonic transmission and reception method, by setting the width of the ultrasonic beam broader than usual as described above, a spare time of 48 msec is provided corresponding to the transmission halt period, and therefore, an image signal for one frame are generated in the ultrasonic diagnostic apparatus main body in the period, and an ultrasonic diagnostic image can be displayed according to the display rate set by the display timing control unit 364 (FIG. 2).

Further, when an error occurs in transfer of raw data, by transmitting a retransfer request from the ultrasonic diagnostic apparatus main body 2 to the ultrasonic probe 1, the raw data can be retransferred from the ultrasonic probe 1 to the ultrasonic diagnostic apparatus main body 2.

FIG. 12C shows a modified example of the ultrasonic transmission and reception method used in the ultrasonic diagnostic apparatus according to the second embodiment of the present invention. In the modified example as shown in FIG. 12C, one area contains six sampling points in a radial direction ("R" direction in the drawing) and five sampling points in a deviation direction ("θ" direction in the drawing). Here, raw data of at least one frame obtained based on reception signals outputted from the plural ultrasonic transducers 10 is stored in the data storage unit 35, and therefore, raw data obtained by plural transmissions can be used for generating one sound ray signal.

In the case where ultrasonic beams are sequentially transmitted such that adjacent two areas overlap with each other as shown in FIG. 12C, one sound ray signal can be generated by performing signal processing with respect to one sampling point within a region, in which the adjacent two areas overlap with each other, by using raw data obtained by plural transmissions. For example, when one sound ray signal is calculated by performing signal processing by using raw data obtained by plural transmissions, an SN ratio can be improved, or resolving power reduced due to broadening of an aperture can be improved. Alternatively, when plural sound ray signals with respect to one sampling point are generated respectively based on raw data obtained by plural transmissions, and then, an average value of those sound ray signals is obtained, one sound ray signal can be obtained in which SN ratio is improved or resolving power that has been reduced due to broadening of the aperture is improved.

In the case where ultrasonic beams are sequentially transmitted such that adjacent two areas overlap with each other as described above, it is necessary to perform signal processing while reflecting information on a size of an overlap portion (for example, the number of the sampling points) of the adjacent two areas. Accordingly, the control unit 42 of the ultrasonic diagnostic apparatus main body 2 as shown in FIG. 2 controls the image forming unit 36 to generate an image signal while reflecting the information on the size of the overlap portion of the adjacent two areas. Alternatively, the control unit 42 may control the data storage unit 35 to store the information on the size of the overlap portion together with the raw data, and thereby, the image forming unit 36 reads out the information and generates an image signal while reflecting the information.

In the above description, the case where an image signal of one frame represents one sectional image has been explained. However, when a three-dimensional image is formed, an image signal of one frame may represent one three-dimensional image.

Referring to FIG. 2 again, the control unit 42 controls the transmission control unit 12 via the control unit 22 of the ultrasonic probe 1 as shown in FIG. 1 to change sizes of plural areas covered by ultrasonic beams sequentially transmitted from the plural ultrasonic transducers, and thereby, can change the data volume to be transmitted from the ultrasonic probe 1.

Figure 13A:
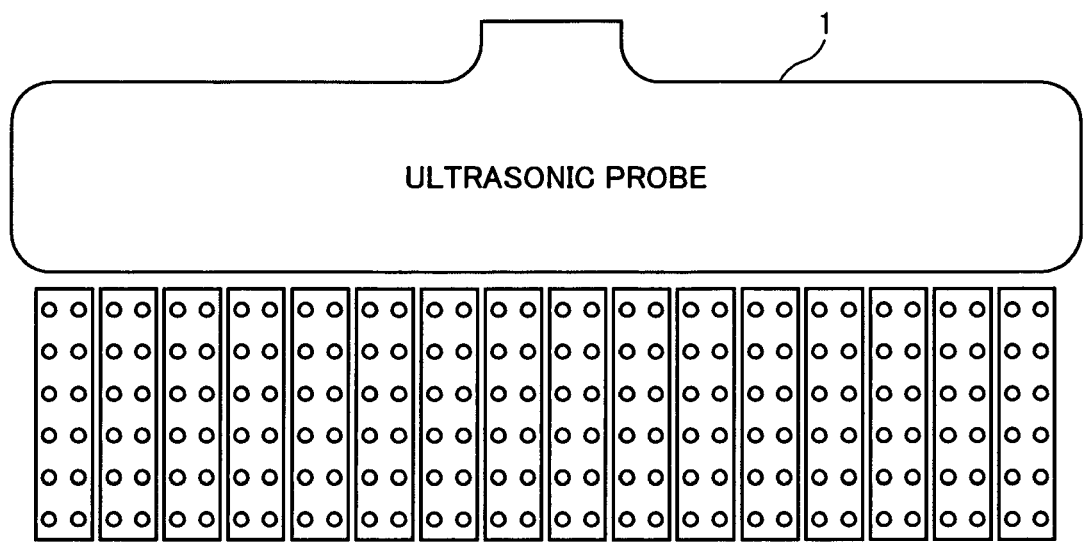
FIGS. 13A and 13B show an example of changing sizes of plural areas covered by sequentially transmitted ultrasonic beams.

For example, in a normal mode as shown in FIG. 13A, ultrasonic beams are sequentially transmitted from the ultrasonic probe 1 toward 16 areas at 0.2 msec intervals in one frame period. Accordingly, the time required for transmission and reception of ultrasonic waves per one frame is 3.2 msec. On the other hand, the control unit 42 changes operation of the ultrasonic probe 1 into a transmission time shortening mode, in which a transmission time is made shorter than that in the normal mode, according to imaging condition (for example, in the case of imaging a part, in which the tissue moves quickly, such as a heart) or instruction of the operator.

Figure 13B:
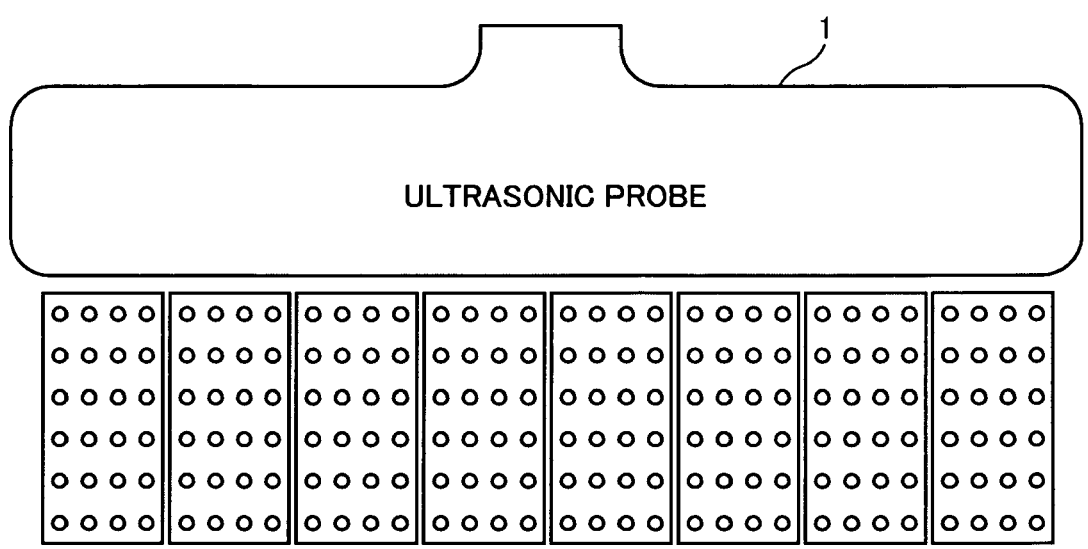

In the transmission time shortening mode as shown in FIG. 13B, for example, ultrasonic beams are sequentially transmitted from the ultrasonic probe 1 toward 8 areas at 0.2 msec intervals in one frame period. Accordingly, the time required for transmission and reception of ultrasonic waves per one frame becomes 1.6 msec. Since the ultrasonic wave transmission time in one frame period becomes shorter (the transmission halt period becomes longer) by performing the above-mentioned control, the ultrasonic diagnostic apparatus becomes more advantageous to imaging of a part in which the tissue moves quickly and retransmission of the raw data from the ultrasonic probe 1 to the ultrasonic diagnostic apparatus main body 2 in the case where an error occurs in transfer of the raw data.

Further, with change of sizes of plural areas forming one frame, a size of an overlap portion (for example, the number of the sampling points) of adjacent two areas covered by ultrasonic beams sequentially transmitted may be appropriately changed between frames.

Figure 14A:
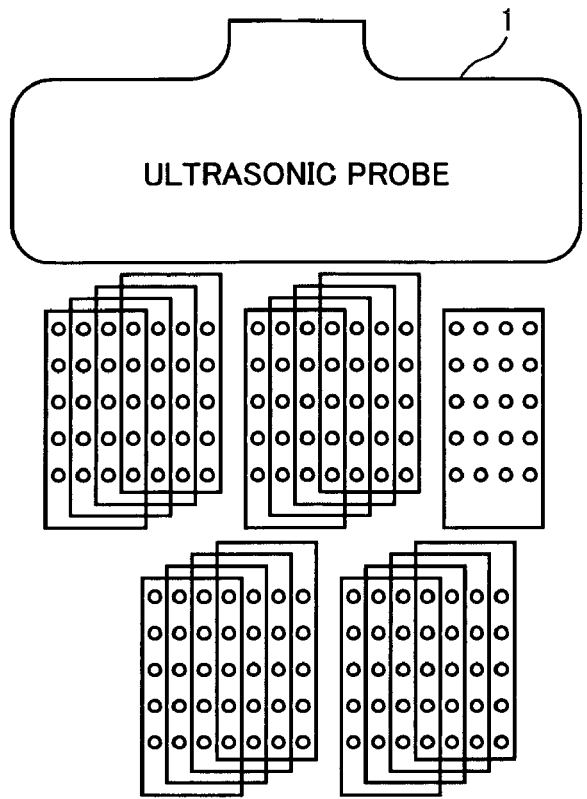
FIGS. 14A and 14B show an example of changing a size of an overlap portion of adjacent two areas among frames.

For example, in the normal mode as shown in FIG. 14A, it is set that ultrasonic beams are sequentially transmitted from the ultrasonic probe 1 in 17 directions (toward 17 areas) at 0.2 msec intervals in one frame period and the adjacent two areas overlap with each other by 75%. Accordingly, the time required for transmission and reception of ultrasonic waves per one frame is 3.4 msec. On the other hand, the control unit 42 changes operation of the ultrasonic probe 1 into the transmission time shortening mode, in which a transmission time is made shorter than that in the normal mode, according to imaging condition (for example, in the case of imaging a part, in which the tissue moves quickly, such as a heart) or instruction of the operator.

Figure 14B:
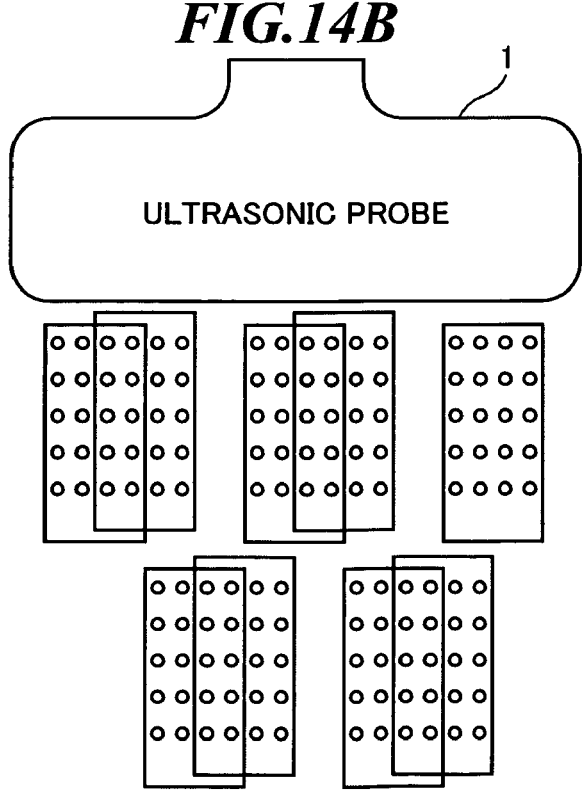

In the transmission time shortening mode as shown in FIG. 14B, for example, it is set that ultrasonic beams are sequentially transmitted from the ultrasonic probe 1 in 9 directions (toward 9 areas) at 0.2 msec intervals in one frame period and the adjacent two areas overlap with each other by 50%. Accordingly, the time required for transmission and reception of ultrasonic waves per one frame becomes 1.8 msec. Since the ultrasonic wave transmission time in one frame period becomes shorter (the transmission halt period becomes longer) by performing the above-mentioned control, the ultrasonic diagnostic apparatus becomes more advantageous to imaging of a part in which the tissue moves quickly and retransmission of the raw data from the ultrasonic probe 1 to the ultrasonic diagnostic apparatus main body 2 in the case where an error occurs in transfer of the raw data.

Further, the control unit 42 controls the parallel/serial conversion unit 16 via the control unit 22 of the ultrasonic probe 1 as shown in FIG. 1 to change the number of ultrasonic transducers to be used for reception of ultrasonic echoes, and thereby, can change the data volume to be transmitted from the ultrasonic probe 1. Therefore, by combining the same ultrasonic probe with various ultrasonic diagnostic apparatus main bodies, ultrasonic diagnostic apparatuses for intended image quality, system scale, and cost can be constructed.

For example, in the case where the ultrasonic probe is combined with an ultrasonic diagnostic apparatus main body having specialized hardware and high processing capability, the number of transmissions may be set to 128 and the number of elements to be used for reception may be set to 128. On the other hand, in the case where the ultrasonic probe is combined with an ultrasonic diagnostic apparatus main body having a general-purpose computer and a small display unit for giving priority to downsizing and cost, the number of transmissions may be set to 32 and the number of elements to be used for reception may be set to 24. As an intermediate case of them, the number of transmissions may be set to 64 and the number of elements to be used for reception may be set to 64.

Figure 15:
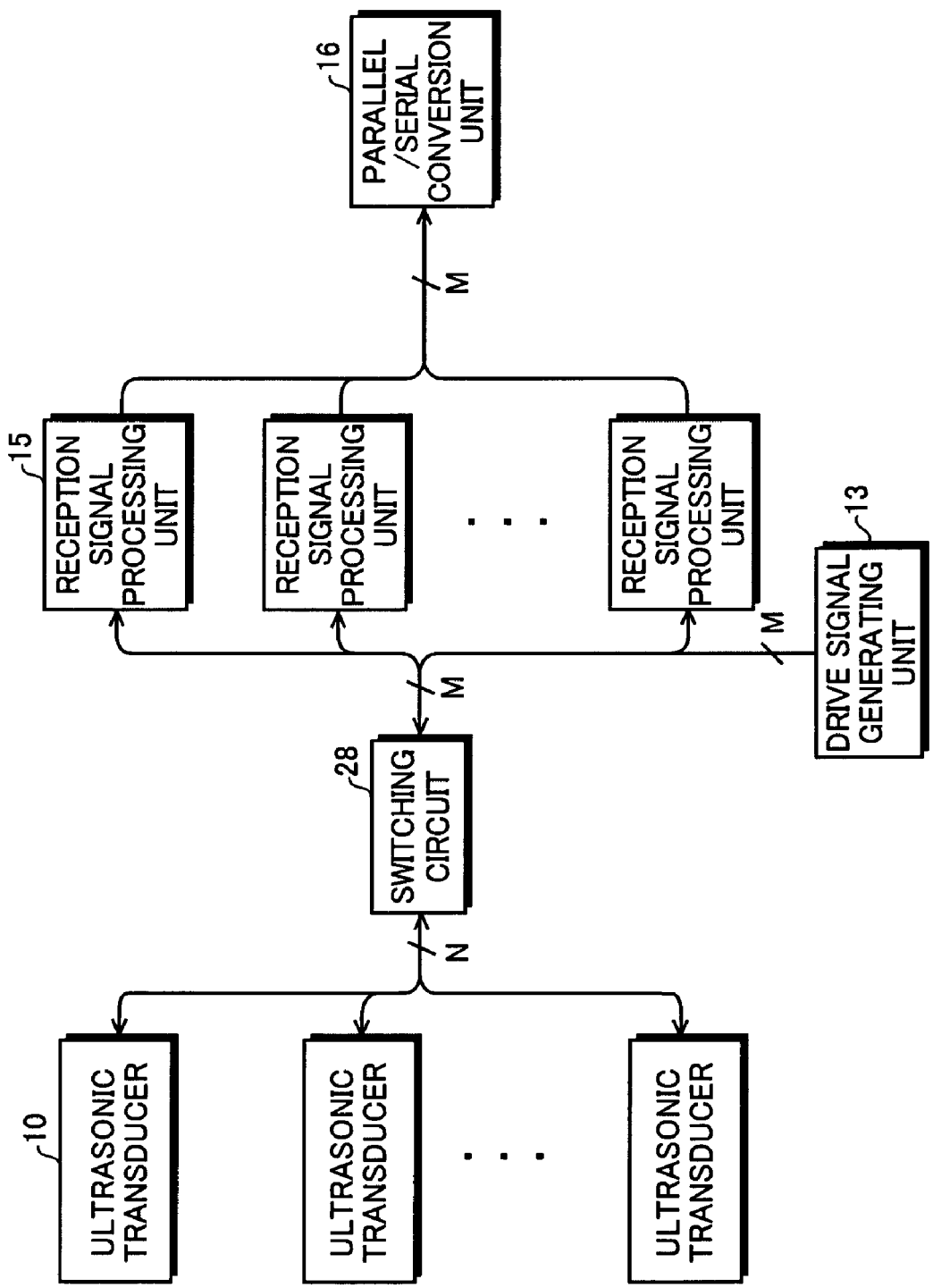
FIG. 15 is a block diagram showing a first modified example of the ultrasonic probe shown in FIG. 1.

FIG. 15 is a block diagram showing a first modified example of the ultrasonic probe as shown in FIG. 1. In the first modified example as shown in FIG. 15, a switching circuit 28 for switching connection relations between the plural ultrasonic transducers 10 and transmission and reception circuits ("M" transmission circuits within the drive signal generating unit 13 and "M" reception signal processing circuits 15) provided in the ultrasonic probe is added to the ultrasonic probe as shown in FIG. 1. The rest of the configuration is the same as that of the ultrasonic probe as shown in FIG. 1.

Generally, in the ultrasonic probe of a linear-scan type or a convex-scan type, the object is scanned while aperture in transmission and reception is sequentially switched. Given that the number of ultrasonic transducers provided in the ultrasonic probe is "N" and the number of ultrasonic transducers to be used at the same time is "M" (M<N), the switching circuit 28 selects "M" ultrasonic transducers from the "N" ultrasonic transducers and connects the selected "M" ultrasonic transducers to the "M" transmission and reception circuits, respectively. Thereby, the number of transmission and reception circuits can be reduced compared to the ultrasonic probe as shown in FIG. 1.

Figure 16:
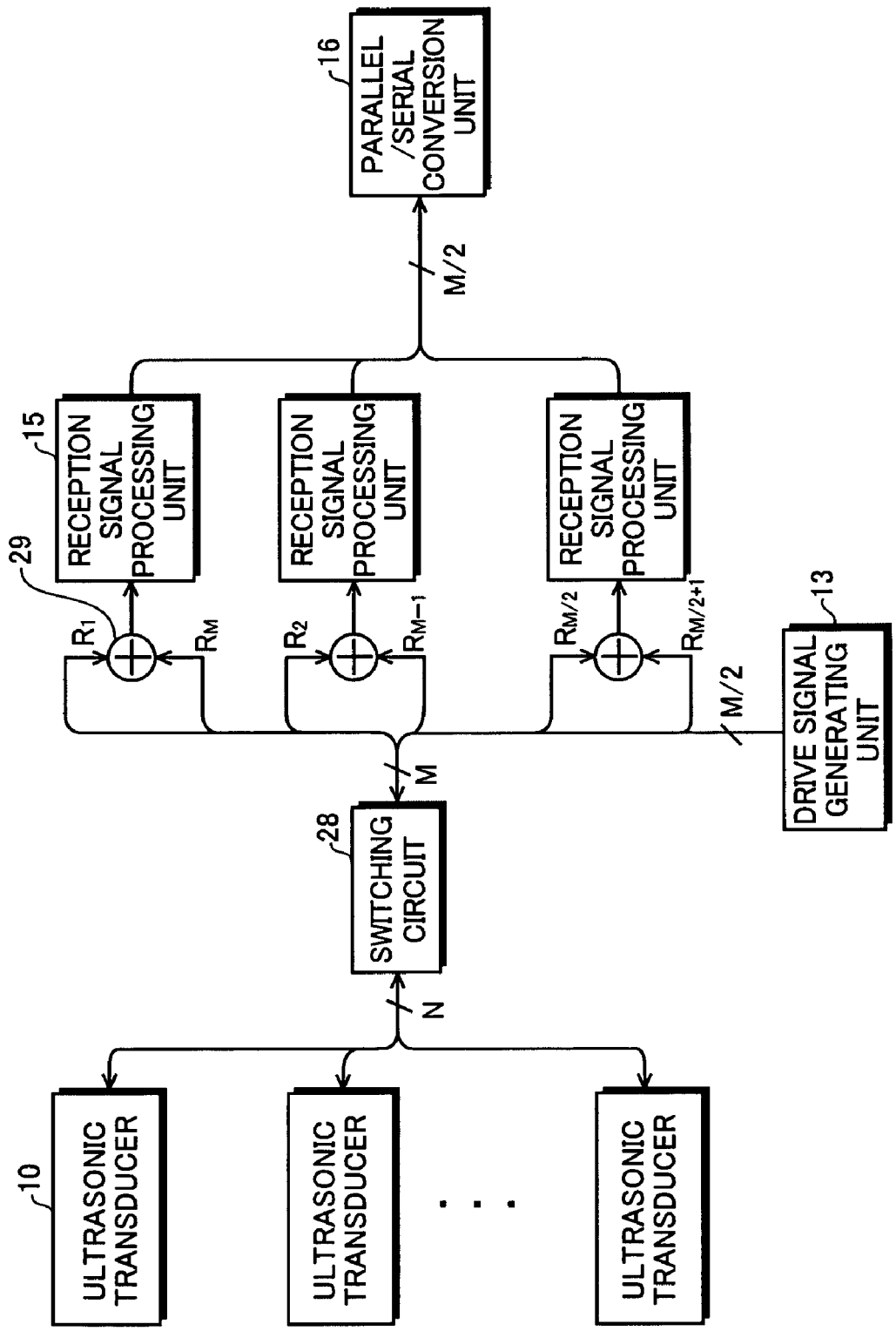
FIG. 16 is a block diagram showing a second modified example of the ultrasonic probe shown in FIG. 1.

FIG. 16 is a block diagram showing a second modified example of the ultrasonic probe as shown in FIG. 1. In the second modified example as shown in FIG. 16, addition circuits 29 for adding the reception signals outputted from two ultrasonic transducers 10 at reception of ultrasonic waves are added to the first modified example as shown in FIG. 15. At the transmission of ultrasonic waves, each transmission circuit included in the drive signal generating unit 13 supplies one drive signal to the two ultrasonic transducers 10 in parallel. The rest of the configuration is the same as that of the ultrasonic probe as shown in FIG. 1.

Generally, in the ultrasonic probe of a linear-scan type or a convex-scan type, the transmission and reception directions are perpendicular to the arrangement surface of the ultrasonic transducers, and thus, the amounts of delay in transmission and reception are symmetric with respect to the ultrasonic beam. Therefore, in the transmission and reception aperture formed of the "M" ultrasonic transducers, the amounts of delay are equal to each other between the first ultrasonic transducer and the Mth ultrasonic transducer, and therefore, the reception signal $R_1$ and the reception signal $R_M$ may be added to each other or the drive signal may be used in common. Similarly, since the amounts of delay are equal to each other between the second ultrasonic transducer and the (M-1)th ultrasonic transducer, and therefore, the reception signal $R_2$ and the reception signal $R_{M-1}$ may be added to each other or the drive signal may be used in common. Thereby, the number of reception signal processing units 15 can be reduced to the half compared to that of the first modified example as shown in FIG. 15, and further, the transfer bit rate between the ultrasonic probe and the ultrasonic diagnostic apparatus main body can be reduced to the half.

In the above-mentioned embodiments, the case where wireless communication is performed between the ultrasonic probe and the ultrasonic diagnostic apparatus main body has been explained. However, wired communication may be performed between the ultrasonic probe and the ultrasonic diagnostic apparatus main body. In this case, the number of signal lines connecting the ultrasonic probe to the ultrasonic diagnostic apparatus main body can be reduced. Further, the power supply voltage of the ultrasonic probe may be supplied from the ultrasonic diagnostic apparatus main body.

The invention claimed is:

1. An ultrasonic diagnostic apparatus comprising:
an ultrasonic probe including plural ultrasonic transducers configured to transmit an ultrasonic beam according to drive signals and configured to receive ultrasonic echoes to output reception signals, reception signal processing units configured to generate parallel sample data based on the reception signals outputted from said plural ultrasonic transducers, a parallel/serial conversion unit configured to convert the parallel sample data generated by said reception signal processing units into serial sample data, a communication unit configured to wirelessly transmit the sample data converted by said parallel/serial conversion unit, a memory configured to temporarily store the sample data converted by said parallel/serial conversion unit, and a control unit configured to control said communication unit to transmit the sample data read out from said memory in response to a retransmission request; and
an ultrasonic diagnostic apparatus main body including a storage unit configured to store the sample data of at least one frame transmitted from said ultrasonic probe, an image forming unit configured to generate an image signal by performing reception focusing processing on the sample data with respect to every one frame read out from said storage unit, a reception status detecting unit configured to detect a reception status of the sample data transmitted from said ultrasonic probe based on an error rate of the sample data, and a second communication unit configured to transmit the retransmission request to said ultrasonic probe when the reception status detected by said reception status detecting unit is not better than a predetermined level.

2. The ultrasonic diagnostic apparatus according to claim 1, wherein:
said ultrasonic diagnostic apparatus main body further includes a serial/parallel conversion unit configured to convert the serial sample data transmitted from said ultrasonic probe into parallel sample data; and
said storage unit is provided at a subsequent stage of said serial/parallel conversion unit, and configured to store the parallel sample data.

3. The ultrasonic diagnostic apparatus according to claim 1, wherein:
said ultrasonic diagnostic apparatus main body further includes a serial/parallel conversion unit configured to convert the serial sample data transmitted from said ultrasonic probe into parallel sample data; and
said storage unit is provided at a former stage of said serial/parallel conversion unit, and configured to store the serial sample data.

4. The ultrasonic diagnostic apparatus according to claim 1, wherein said ultrasonic probe further includes a drive signal generating unit configured to generate the drive signals such that adjacent two areas covered by ultrasonic beams sequentially transmitted from said plural ultrasonic transducers overlap with each other.

5. The ultrasonic diagnostic apparatus according to claim 4, wherein said ultrasonic diagnostic apparatus main body further includes a second control unit configured to change data volume transmitted from said ultrasonic probe by controlling said drive signal generating unit to change sizes of plural areas covered by ultrasonic beams sequentially transmitted from said plural ultrasonic transducers.

6. The ultrasonic diagnostic apparatus according to claim 5, wherein said control unit is configured to control said image forming unit to generate the image signal while reflecting information on a size of an overlap portion of the adjacent two areas.

7. The ultrasonic diagnostic apparatus according to claim 5, wherein said storage unit is configured to store information on a size of an overlap portion of the adjacent two areas, and, said image forming unit is configured to generate the image signal while reflecting the information on the size of the overlap portion of the adjacent two areas.

8. The ultrasonic diagnostic apparatus according to claim 1, wherein said ultrasonic diagnostic apparatus main body further includes a second control unit configured to change data volume transmitted from said ultrasonic probe by controlling said parallel/serial conversion unit to change a number of ultrasonic transducers to be used for receiving the ultrasonic echoes.

9. The ultrasonic diagnostic apparatus according to claim 1, wherein each of said reception signal processing units includes:
a signal preprocessing unit configured to perform one of quadrature detection processing and quadrature sampling processing on the reception signal outputted from respective one of said plural ultrasonic transducers to generate a complex baseband signal; and
a sampling unit configured to sample the complex baseband signal generated by said signal preprocessing unit to generate the sample data.

10. The ultrasonic diagnostic apparatus according to claim 9, wherein said signal preprocessing unit includes:
a preamplifier configured to amplify the reception signal outputted from respective one of said plural ultrasonic transducers;
a low-pass filter configured to limit a frequency band of the reception signal outputted from said preamplifier;
an analog/digital converter configured to convert an analog reception signal outputted from said low-pass filter into a digital reception signal; and
a quadrature detection processing unit configured to perform quadrature detection processing on the digital reception signal converted by said analog/digital converter to generate the complex baseband signal.

11. The ultrasonic diagnostic apparatus according to claim 9, wherein said signal preprocessing unit includes:
a preamplifier configured to amplify the reception signal outputted from respective one of said plural ultrasonic transducers;
a low-pass filter configured to limit a frequency band of the reception signal outputted from said preamplifier;
an analog/digital converter configured to convert an analog reception signal outputted from said low-pass filter into a digital reception signal;
a quadrature sampling unit configured to perform quadrature sampling processing on the digital reception signal converted by said analog/digital converter to generate a first signal sequence and a second signal sequence; and
a second low-pass filter configured to limit frequency bands of the first and second signal sequences generated by said quadrature sampling unit to generate the complex baseband signal.

12. The ultrasonic diagnostic apparatus according to claim 9, wherein said sampling unit is configured to alternately and time-divisionally sample two signals included in the complex baseband signal generated by said signal preprocessing unit.

13. The ultrasonic diagnostic apparatus according to claim 1, wherein said ultrasonic probe further includes a circuit configured to change connection relations between said plural ultrasonic transducers and said reception signal processing units.

14. An ultrasonic diagnostic apparatus comprising:
an ultrasonic probe including plural ultrasonic transducers configured to transmit a broad ultrasonic beam covering a tissue area within an object to be inspected according to drive signals and configured to receive ultrasonic echoes reflected from the tissue area within the object to output reception signals, a drive signal generating unit configured to generate the drive signals, a reception signal processing unit configured to generate parallel raw data including information on the tissue area based on the reception signals outputted from said plural ultrasonic transducers, a parallel/serial conversion unit configured to convert the parallel raw data generated by said reception signal processing unit into serial raw data, and a communication unit configured to wirelessly transmit the raw data converted by said parallel/serial conversion unit; and
an ultrasonic diagnostic apparatus main body including an image forming unit configured to generate an image signal by performing reception focusing processing on the raw data transmitted from said ultrasonic probe, and a control unit configured to control said drive signal generating unit to change sizes of plural areas covered by ultrasonic beams sequentially transmitted from said plural ultrasonic transducers and thereby change time required for transmission and reception of ultrasound waves per one frame.

15. The ultrasonic diagnostic apparatus according to claim 14, wherein said ultrasonic diagnostic apparatus main body further includes a storage unit configured to store the raw data transmitted from said ultrasonic probe.

16. The ultrasonic diagnostic apparatus according to claim 15, wherein said storage unit is configured to store raw data of at least one frame, and said image forming unit is configured to generate the image signal by performing reception focusing processing on the raw data with respect to every one frame read out from said storage unit.

17. The ultrasonic diagnostic apparatus according to claim 14, wherein said control unit is configured to control said drive signal generating unit to generate the drive signals such that adjacent two areas covered by ultrasonic beams sequentially transmitted from said plural ultrasonic transducers overlap with each other.

18. The ultrasonic diagnostic apparatus according to claim 14, wherein said control unit is configured to control said image forming unit to generate the image signal while reflecting information on a size of an overlap portion of the adjacent two areas.

19. The ultrasonic diagnostic apparatus according to claim 14, wherein said ultrasonic diagnostic apparatus main body further includes a storage unit configured to store information on a size of an overlap portion of the adjacent two areas, and said image forming unit is configured to generate the image signal while reflecting the information on the size of the overlap portion of the adjacent two areas.

20. The ultrasonic diagnostic apparatus according to claim 14, wherein said control unit is configured to control said drive signal generating unit to change a size of an overlap portion of adjacent two areas among frames, said adjacent two areas being covered by ultrasonic beams sequentially transmitted from said plural ultrasonic transducers.

21. The ultrasonic diagnostic apparatus according to claim 14, wherein said ultrasonic diagnostic apparatus main body wherein said control unit is configured to change data volume transmitted from said ultrasonic probe by controlling said parallel/serial conversion unit to change a number of ultrasonic transducers to be used for receiving the ultrasonic echoes.

* * * * *